US011998550B2

(12) United States Patent
Rosenbloom et al.

(10) Patent No.: US 11,998,550 B2
(45) Date of Patent: *Jun. 4, 2024

(54) TRAMETINIB PREVENTS MESOTHELIAL-MESENCHYMAL TRANSITION AND AMELIORATES ABDOMINAL ADHESION AND PULMONARY FIBROSIS FORMATION

(71) Applicant: Thomas Jefferson University, Philadephia, PA (US)

(72) Inventors: Joel Rosenbloom, Wynnewood, PA (US); Edward John Macarak, Chadds Ford, PA (US)

(73) Assignee: THOMAS JEFFERSON UNIVERSITY, Philadelphia, PA (US)

(*) Notice: Subject to any disclaimer, the term of this patent is extended or adjusted under 35 U.S.C. 154(b) by 227 days.

This patent is subject to a terminal disclaimer.

(21) Appl. No.: 16/607,032

(22) PCT Filed: Apr. 20, 2018

(86) PCT No.: PCT/US2018/028516
§ 371 (c)(1),
(2) Date: Oct. 21, 2019

(87) PCT Pub. No.: WO2018/195392
PCT Pub. Date: Oct. 25, 2018

(65) Prior Publication Data
US 2020/0046708 A1 Feb. 13, 2020

Related U.S. Application Data

(60) Provisional application No. 62/487,802, filed on Apr. 20, 2017.

(51) Int. Cl.
*A61K 31/519* (2006.01)
*A61K 9/12* (2006.01)
(Continued)

(52) U.S. Cl.
CPC .............. *A61K 31/519* (2013.01); *A61K 9/12* (2013.01); *A61P 11/00* (2018.01); *A61P 41/00* (2018.01)

(58) Field of Classification Search
CPC .............................. A61K 31/519; A61P 41/00
See application file for complete search history.

(56) References Cited

U.S. PATENT DOCUMENTS

2007/0172856 A1  7/2007  Hogaboam et al.
2008/0063682 A1  3/2008  Cashman et al.
(Continued)

FOREIGN PATENT DOCUMENTS

WO   WO-2014193898 A1 * 12/2014 ........... A61K 31/506

OTHER PUBLICATIONS

Kelley; "Dabrafenib Alone and in Combination With Trametinib Before Surgery in Treating Patients . . . That Can Be Removed By Surgery"; NCT01701037; first posted 2012; ClinicalTrials.gov; https://clinicaltrials.gov/ct2/history/NCT01701037?V_1=View#StudyPage; accessed Oct. 15, 2021 (Year: 2012).*

(Continued)

*Primary Examiner* — Timothy P Thomas
(74) *Attorney, Agent, or Firm* — Cozen O'Connor

(57) ABSTRACT

A method of reducing the severity of abdominal adhesion due to surgical complications comprising: administering to said patient at least a first dose of trametinib between 0.01 mg to 2.0 mg, and after said surgical procedure, administering to said patient a further dose of trametinib between 0.01 mg to 2.0 mg, daily, for at least seven days post-surgery.

3 Claims, 19 Drawing Sheets

(51) Int. Cl.
*A61P 11/00* (2006.01)
*A61P 41/00* (2006.01)

(56) References Cited

U.S. PATENT DOCUMENTS

2013/0109705 A1   5/2013   Gilmer et al.
2017/0100345 A1   4/2017   Ribas et al.

OTHER PUBLICATIONS

M.D. Anderson Cancer Center (ClinicalTrials.gov NCT02231775; "Dabrafenib and Trametinib Before and After Surgery in Treating Patients With Stage IIIB-C Melanoma With Braf V600 Mutation"; first posted Sep. 4, 2014; https://clinicaltrials.gov/ct2/show/NCT02231775, accessed Oct. 15, 2021 (Year: 2014).*

Kelley; "Dabrafenib Alone and in Combination With Trametinib Before Surgery in Treating Patients With Locally or Regionally Advanced Melanoma That Can Be Removed By Surgery"; NCT01701037; first posted 2012; ClinicalTrials.gov; https://clinicaltrials.gov/ct2/history/NCT01701037?V_1=View#StudyPageTop (Year: 2012).*

M.D. Anderson Cancer Center; ClinicalTrials.gov NCT02231775; "Dabrafenib and Trametinib Before and After Surgery in Treating Patients With Stage IIIB-C Melanoma With Braf V600 Mutation"; first posted Sep. 4, 2014; https://clinicaltrials.gov/ct2/show/NCT02231775 (Year: 2014).*

Uppaluri et al.; "Biomarker and Tumor Responses of Oral Cavity Squamous Cell Carcinoma to Trametinib: A Phase II Neoadjuvant Window-of-Opportunity Clinical Trial"; Apr. 1, 2017; @2016; Clin. Cancer Res .; 23(9); 2186-94; doi: 10.1158/1078-0432.CCR-16-1469 (Year: 2017).*

Bellini, A., et al., "The role of the fibrocyte, a bone marrow-derived mesenchymal progenitor, in reactive and reparative fibrosis", Laboratory Investigation, vol. 87, No. 9, pp. 858-870, 2007.

Bhattacharyya, S., et al., "Understanding fibrosis in systemic sclerosis: shifting paradigms, emerging opportunities", Nature Reviews Rheumatology, vol. 8, No. 1, pp. 42-54, 2011.

Cheong, Y.C., et al., "IL-1, IL-6 and TNF-alpha concentrations in the peritoneal fluid of women with pelvic adhesions" Hum Reprod, vol. 17, No. 1, pp. 69-75, 2002.

Duscher, D., et al., "Mechanotransduction and fibrosis", Journal of Biomechanics, vol. 47, No. 9, pp. 1997-2005, 2014.

Falk, P., et al., "Studies of TGF-β1-3 in Serosal Fluid during Abdominal Surgery and Their Effect on In Vitro Human Mesothelial Cell Proliferation", Journal of Surgical Research, vol. 154, No. 2, pp. 312-316, 2009.

Fang, C.C., et al., "Fibrin-Induced Epithelial-to-Mesenchymal Transition of Peritoneal Mesothelial Cells as a Mechanism of Peritoneal Fibrosis: Effects of Pentoxifylline", PLos One, vol. 7, No. 9, Article No. e44765, 11 pages, 2012.

Femel, J., et al., "Therapeutic vaccination against fibronectin ED-A attenuates progression of metastatic breast cancer", Oncotarget, vol. 5, No. 23, p. 12418-12427, 2014.

Ignotz, R.A., et al., "Transforming growth factor-beta stimulates the expression of fibronectin and collagen and their incorporation into the extracellular matrix", The Journal of Biological Chemistry, vol. 261, No. 9, pp. 4337-4345, 1986.

Ignotz, R.A., et al., "Regulation of fibronectin and type I collagen mRNA levels by transforming growth factor-beta", The Journal of Biological Chemistry, vol. 262, No. 14, pp. 6443-6446, 1987.

International Search Report and Written Opinion dated Jun. 27, 2018 in International Application No. PCT/US2018/028516.

Jin, X., et al., "Paradoxical effects of short- and long-term interleukin-6 exposure on liver injury and repair", Hepatology, vol. 43, No. 3, pp. 474-484, 2006.

Jin, X., et al., "Interleukin-6 inhibits oxidative injury and necrosis after extreme liver resection", Hepatology, vol. 46, No. 3, pp. 802-812, 2007.

Jin, X., et al., "Interleukin-6 is an important in vivo inhibitor of intestinal epithelial cell death in mice", Gut, vol. 59, No. 2, pp. 186-196, 2008.

Jin, X., et al., "Pathobiological mechanisms of peritoneal adhesions: The mesenchymal transition of rat peritoneal mesothelial cells induced by TGF-1 and IL-6 requires activation of Erk 1/2 and Smad2 linker region phosphorylation", Matrix Biology, vol. 51, pp. 55-64, 2016.

Kalluri, R., et al., "Epithelial-mesenchymal transition and its implications for fibrosis", The Journal of clinical investigation, vol. 112, No. 12, pp. 1776-1784, 2003.

Liu, Q., et al., "A Crosstalk between the Smad and JNK Signaling in the TGF-β-Induced Epithelial-Mesenchymal Transition in Rat Peritoneal Mesothelial Cells", PLoS One, vol. 7, No. 2, Article No. e32009, 9 pages, 2012.

Macarak, E., et al., "Trametinib prevents mesothelial-mesenchymal transition and ameliorates abdominal adhesion formation", Journal of Surgical Research, vol. 227, pp. 198-210, 2018.

McFadyen, M.P., et al., "Differences among eight inbred strains of mice in motor ability and motor learning on a rotorod", Genes, Brain and Behavior, vol. 2, No. 4, pp. 214-219, 2003.

Panahi, F., et al., "Macroscopic and pathological assessment of methylene blue and normal saline on postoperative adhesion formation in a rat cecum model", International Journal of Surgery (London, England), vol. 10, No. 9, pp. 537-541, 2012.

Postlethwaite, A.E., et al., "Cellular origins of fibroblasts: possible implications for organ fibrosis in systemic sclerosis", Current Opinion in Rheumatology, vol. 16, No. 6, pp. 733-738, 2004.

Roberts, A.B., et al., "Transforming growth factor type beta: rapid induction of fibrosis and angiogenesis in vivo and stimulation of collagen formation in vitro", Proc. Natl. Acad. Sci. USA, vol. 83, No. 12, pp. 4167-4171, 1986.

Thiery, J.P., et al., "Complex networks orchestrate epithelial-mesenchymal transitions", Nature Reviews Molecular Cell Biology, vol. 7, No. 2, pp. 131-142, 2006.

Thiery, J.P., et al., "Epithelial-mesenchymal transitions in development and disease", Cell, vol. 139, No. 5, pp. 871-890, 2009.

Tomasek, J.J., et al., "Myofibroblasts and mechano-regulation of connective tissue remodeling", Nature Reviews Molecular Cell Biology, vol. 3, No. 5, pp. 349-363, 2002.

Xu, X., et al., "Role of mast cells and myofibroblasts in human peritoneal adhesion formation", Annals of Surgery, vol. 236, No. 5, pp. 593-601, 2002.

\* cited by examiner

TRAMETINIB PREVENTS MESOTHELIAL-MESENCHYMAL TRANSITION AND AMELIORATES ABDOMINAL ADHESION AND PULMONARY FIBROSIS FORMATION

CROSS REFERENCE TO RELATED APPLICATIONS

This application is a National Phase Stage of International Application No. PCT/US2018/28516, filed Apr. 20, 2018, which claims priority to U.S. Provisional Patent Application No. 62/487,802, filed Apr. 20, 2017.

FIELD OF INVENTION

This application is generally related to methods of treatment of fibrosis, abdominal adhesions and pulmonary fibrosis through administration of therapeutics.

BACKGROUND OF INVENTION

While peritoneal adhesions may be caused by infection, inflammation or ischemia, surgical procedures are the primary cause since 90% of patients will develop adhesions after abdominal surgery. Between 1998 and 2002, over 18% of hospital admissions were secondary to abdominal adhesions alone at a cost greater than 1 billion dollars. Such adhesions are responsible for pelvic pain, bowel obstruction and infertility. Although modern advances in surgical technique, including laparoscopy, have led to a decrease in their incidence, intestinal adhesions still pose a very significant medical as well as economic problem.

Unfortunately, adequate therapeutic solutions have proven elusive. Successful treatment of fibrotic reactions is bedeviled by several confounding factors, not the least of which is their complex pathogenesis. Whatever the cause, the process of adhesion formation can be broken down into several stages which are as follows.

In abdominal adhesion formation, there are three stages with the first being coagulation, a critical factor in adhesion pathogenesis. Studies have shown that coagulation involves a number of protein factors and reactions which either facilitate or inhibit the ultimate formation of a fibrin clot. While, in many cases, the formation of a clot is essential to limit injury, resolution of the clot, in a timely manner, is necessary to prevent adhesion formation. Thus, the balance between fibrin clot formation and its lysis is critical and provides a rational basis for enhancing clot lysis as a therapeutic strategy. However, in practice, this has proven difficult.

The next stage involves the influx of inflammatory cells consisting of multiple cell types and production of a variety of cytokines and factors and which is elicited by a number of inciting events. This has led to attempts to inhibit inflammation as a therapeutic approach to prevent adhesion or fibrosis formation. By and large, this approach has proven to be unsuccessful.

The final stage in the adhesion process is formation of a connective tissue scar. By and large this stage, which is of critical importance since it is this fibrous scar tissue that causes the most severe complications, has received insufficient attention. This is particularly significant since it is highly likely that connective tissue adhesion formation shares many attributes with fibrotic reactions found elsewhere in the body, including systemic ones such as occur in patients with scleroderma and those affecting individual organs including lung, heart, liver and kidney.

Fibrotic lung fibrosis is characterized by histopathological changes in lung architecture, which is characterized by the replacement of pre-existing alveolar structure by permanent fixed scar tissue. Idiopathic pulmonary fibrosis (IPF), in particular, is a pathology of unknown cause and is a type of interstitial lung disease. It is defined clinically by the radiographic appearance of usual interstitial pneumonia on high-resolution computed tomography (HRCT) scan and/or the histologic appearance of usual interstitial pneumonia upon lung biopsy which cannot be traced to common interstitial lung disease risk factors such as occupational exposures to hazardous materials and either connective tissue or autoimmune diseases.

At the cellular level, it is universally appreciated that a particular cell with unique characteristics, the myofibroblast, is responsible, in all incidences, for the replacement of functioning tissue in affected organs, be it mesothelial cells in the gut, alveoli in the lung or nephrons in the kidney, for example, with non-functional scar tissue which disrupts the normal architecture of the affected organs, ultimately leading to their dysfunction and failure.

While the underlying etiology of fibrotic diseases is frequently unknown, certain signaling pathways activated by several cytokines and growth factors undoubtedly play key roles in their pathogenesis. There is little doubt that the TGF-β family (TGF-β1, -β2, -β3) is the critical regulator of the fibrotic response. The intracellular transduction pathways following TGF-β binding to its cognate receptors are complex but critically important—in the fibrotic response.

It is now well-known that although the causes of fibrotic disorders are diverse and causative mechanisms vary widely, they all share important cellular and molecular common features which provide a framework for therapeutic approaches. The mechanisms by which TGF-β and other cytokines activate fibroblasts and stimulate extracellular matrix (ECM) production are incompletely understood, but clearly involve their overproduction in an uncontrolled fashion by myofibroblasts which appears to involve activation of specific intracellular signaling pathways. The MAP kinase ERK1/2 has been identified as a down-stream target of some activation pathways and thus may have a critical role in the pro-fibrotic response to TGF-β. Because of the critical nature of pathway activation by TGF-β, these pathways are potential targets for therapeutic intervention.

Much more information is needed on the cellular and molecular characterization of pro-fibrotic processes that result in adhesion formation in the gut and thickened respiratory membranes in the lung both of which are examples of tissue scars which prevent normal function. Such characterization is critical in order to formulate novel therapeutic approaches.

As noted, the critical cell in the formation of scar tissue is the myofibroblast which produces increased amounts of fibrillar collagens as well as other matrix proteins such as FNEDA and which expresses α-smooth muscle actin (αSMA), a molecular marker of activated myofibroblasts [1]. While the origins of myofibroblasts may differ depending on the affected organ and the initiating event, in the abdominal cavity, they may arise through a process of trans differentiation of mesothelial cells in which these cells lose their specific epithelial phenotypic markers such as expression of E-cadherin and acquire a mesenchymal or myofibroblastic phenotype which include FNEDA and αSMA.

Since its first identification, it has been known that transforming growth factor-β (TGF-β1), a pleiotropic growth factor with a wide and diverse spectrum of biological activities, plays a key role in fibrotic diseases by mediating the formation of myofibroblasts and stimulating the production of extracellular matrix ECM [2-4]. IL-6, another pleiotropic cytokine with a wide range of biological activities. [5-7], in addition to TGF-0, was also found to be elevated in peritoneal fluid during abdominal surgeries [8, 9] thus potentially implicating it in the cascade of events which lead to adhesion formation.

We have previously found that U0126, a MEK1/2 inhibitor not in clinical use, blocked the rat peritoneal mesothelial/mesenchymal transition induced by TGF-β [10].

SUMMARY OF INVENTION

Preferred embodiments herein are directed to methods of treatment of fibrosis in patients through the administration of trametinib to the patient. Certain embodiments are particularly indicated for reducing the occurrence of, preventing, and ameliorating abdominal adhesions. Certain embodiments are further provided for reducing the occurrence of, preventing, and ameliorating pulmonary fibrosis.

In a preferred embodiment, a method of reducing the occurrence of abdominal adhesions in a patient undergoing a surgical procedure comprising administering to said patient at least a first dose of trametinib before a surgical procedure, and after said surgical procedure, administering to said patient a further dose of trametinib, daily, for at least seven days post-surgery. In certain embodiments, the dose of trametinib is between 0.01 mg to 2.0 mg.

In a preferred embodiment, a method of treating abdominal adhesions, comprising administering to a patient who is susceptible to or suffering from an abdominal adhesion an effective amount of trametinib.

In a preferred embodiment, a method of reducing the severity of abdominal adhesion owing to surgical complications comprising: administering to said patient at least a first dose of trametinib between 0.01 mg to 2.0 mg, and after said surgical procedure, administering to said patient a further dose of trametinib between 0.01 mg to 2.0 mg, daily, for at least seven days post-surgery.

In a preferred embodiment, a method of reducing the severity of abdominal adhesion after a surgical procedure comprising: administering to said patient at least a first dose of trametinib between 0.01 mg to 2.0 mg, daily, for at least seven days post-surgery.

In a preferred embodiment, a method of treating pulmonary fibrosis comprising administering to a patient and effective amount of trametinib. A further embodiment is directed to a method of treating pulmonary fibrosis comprising administering to a patient at least a first dose of trametinib of between 0.01 to 2.0 mg, daily, for at least seven days. In certain preferred embodiments, treatment of pulmonary fibrosis comprises a dosing structure lasting at least 30 days, at least 60 days, at least 90 days, or as a permanent medication, given daily to treat, prevent or slow the formation of, or reduce the formation of pulmonary fibrosis.

A preferred embodiment is directed towards a method of reducing the occurrence of abdominal adhesions in a patient undergoing a surgical procedure comprising administering to said patient an effective dose of trametinib, sufficient to prevent the formation of an adhesion. Preferably, the method wherein an effective dose of trametinib comprises between 0.01 mg to 2.0 mg. Preferably, wherein the method comprising administering to said patient at least a first dose of trametinib prior to a surgical procedure of between 0.01 to 2.0 mg.

In a preferred method, further comprising administering to said patient at least a second dose of trametinib after said surgical procedure of trametinib between 0.01 mg to 2.0 mg. Preferably, the method wherein the at least a second dose of trametinib is administered daily, for at least seven days post-surgery.

In a preferred embodiment, a method of reducing the severity of abdominal adhesion due to surgical complications comprising: administering to said patient at least a first dose of trametinib between 0.01 mg to 2.0 mg, and after said surgical procedure, administering to said patient a further dose of trametinib between 0.01 mg to 2.0 mg, daily, for at least seven days post-surgery.

In a preferred embodiment, a method of reducing the severity of abdominal adhesion after a surgical procedure comprising: administering to said patient at least a first dose of trametinib between 0.01 mg to 2.0 mg, daily, for at least seven days post-surgery.

A preferred embodiment of any of the preceding methods, wherein the method blocks a pathway shared by fibrotic responses in other organs such as the lung, liver, kidney, heart and bladder.

A preferred embodiment includes any one of the preceding methods, wherein a first dose is provided between 0.01 to 2.0 mg, and a second dose, is provided so as to maintain a concentration in the blood plasma at therapeutic levels, wherein at least a second dose is provided at an amount less than said first dose.

A preferred embodiment includes any one of the preceding methods, wherein the at least first does is provided in at least one administration of between 0.001 mg/kg body weight of said patient and of between 0.025 mg/kg body weight of said patient. In preferred methods comprising a first and second dose, wherein the at least second dose is provided at a dose lower than the at least first dose.

In a preferred embodiment, providing a first dose of trametinib, wherein the at least first dose is between 0.01 to 1.0 mg.

A preferred embodiment is directed towards an animal model which can be used to test drugs effective in blocking pathways regulating extracellular matrix (ECM) deposition associated with adhesion formation.

A preferred embodiment is directed to a method of treating a patient for development of excessive fibrin formation comprising; administering to a patient an effective amount of trametinib suitable to treat said fibrin formation; taking a biopsy from said patient in an area of possibly fibrin formation and detecting for the presence of αSMA and FNEDA; determining the levels of αSMA or FNEDA to confirm the presence or absence of the presence of myofibroblasts; administering at least an additional second dose of trametinib when αSMA or FNEDA are detected in the sample.

In a preferred embodiment, wherein the effective amount of trametinib is between 0.01 mg to 2.0 mg given to a patient in a 24 hour period.

In a preferred embodiment, wherein the effective amount of trametinib is between 0.001 mg/kg and 0.25 mg/kg body weight.

In a preferred embodiment, a method of treating fibrosis comprising: taking a biopsy from a patient suspected to have fibrosis; determining the presence of αSMA or FNEDA, administering to said patient an effective amount of trametinib when the presence of αSMA or FNEDA are confirmed in the biopsy sample. In a preferred embodiment, wherein the effective amount of trametinib is give as a pharmaceutical composition of between 0.001 mg/kg to 0.25 mg/kg body weight of said patient. A preferred embodiment, wherein the fibrosis is in the lungs, or wherein the fibrosis is in the abdominal cavity.

A preferred embodiment, comprising a method of treating pulmonary fibrosis comprising administering to a patient suffering from or susceptible to formation of pulmonary fibrosis an effective amount of trametinib. In a preferred embodiment, wherein the effective amount is between 0.001 mg/kg to 0.25 mg/kg body weight of the patient. In a preferred embodiment, wherein the effective amount is between 0.01 mg to 2.0 mg. Preferably, in the embodiments, wherein the trametinib is administered in a pharmaceutical composition. Preferably, wherein the pharmaceutical composition is administered as an aerosol, through inhalation to the lungs.

In a preferred embodiment, a method of reducing the formation of pulmonary fibrosis comprising administering to a patient an effective amount of trametinib, wherein said effective amount is between 0.01 mg to 2.0 mg.

DETAILED DESCRIPTION OF THE EMBODIMENTS

Figure 1:
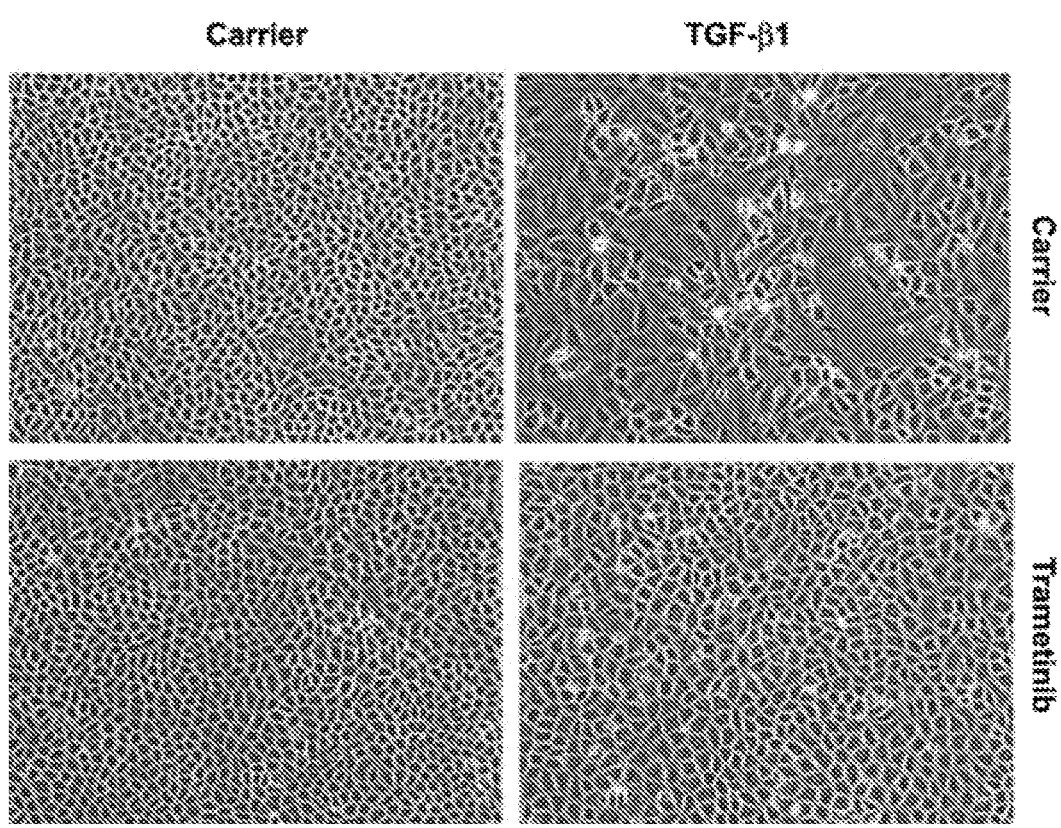
FIG. 1 Cultured rat peritoneal mesothelial cells treated either with TGF-β1 alone or plus trametinib. Cells treated with TGF-β1 alone (upper right panel) show cells transitioning to a fibroblast-like morphology and pro-fibrotic phenotype while cells treated with TGF-β1+trametinib show no such morphological changes (lower right panel).

As used herein, the term "treat" when used in context of treating a disease indicates a delayed onset of disease, reduction in the rate of progression of a disease, reduction in the size of disease formation, reduction on the amount of damaged or diseased tissue. Thus, a treatment may not eliminate all diseased tissue but may stop progression, slow progression, and eliminate some diseased tissue.

As used here, the term "pharmaceutical composition" comprises an active drug ingredient and additional excipients suitable for the particular therapeutic treatment, whether via injection, taken orally, inhalation, or administered to the body cavity via any means known to those of skill in the art. Certain preferred embodiments comprise suitable isotonic injectable, powder or solid or liquids for application to the body, solid or liquid oral forms, nasal, inhalation via aerosols, patches, ointments, solutions, emulsions, and other suitable and known forms for administration.

Adhesion formation and fibrosis are a major cause of post-operative morbidity after abdominal or gynecologic surgery, occurring in up to 93% of patients in some series. However, little is known about the mechanism of the pathogenesis, and, there are no effective treatments or prevention. Here we investigated a mouse model of large intestinal adhesion formation and examined the expression of pro-fibrotic markers in adhesion sites to further study their formation and test an FDA-approved drug to determine its effect(s) on the expression of the same fibrotic markers initially characterized as being associated with adhesion formation.

In the present study we have determined the effect of the MEK1/2 inhibitor, trametinib, which is in clinical use in the treatment of malignant melanoma, on the TGF-β induced rat peritoneal mesothelial/mesenchymal transition (MMT) and abdominal adhesion formation in a mouse model. Trametinib effectively blocked the MMT in vitro and markedly diminished adhesion formation in vivo, likely by inhibiting the activation of Erk1/2 [10]. These findings indicate that trametinib may be a useful drug for the inhibition of adhesion formation and warrant human clinical studies [22].

C57BL/6 mice were used to develop a consistent model of intra-abdominal adhesion formation. Mouse cecums were gently abraded to promote adhesion formation which were subsequently analyzed histologically and immunochemically to characterize the expression of pro-fibrotic genes including (αSMA and FNEDA isoform both of which were examined immunohistochemically and by quantitative polymerase chain reaction (qPCR). Trichrome staining was used to assess collagen deposition, a major protein component found in the ECM at adhesion sites. Consistent intra-abdominal adhesions in mice were achieved by gentle cecal abrasion with mortality rates of <10%. Adhesions were seen as early as post-operative day 1 with extensive adhesions being formed and vascularized by day 5. Expression of the FNEDA isoform first and subsequently αSMA and collagen occurred during adhesion maturation.

The drug trametinib was chosen for in vivo studies because prior in vitro studies from our laboratory have demonstrated its effectiveness in blocking the MMT of rat mesothelium. When the drug trametinib was administered via an osmotic pump implanted during the cecal abrasion surgery, adhesion formation was either absent (no adhesions) or greatly diminished with respect to the initial formation of adhesions as evidenced by the presence of the FNEDA but not αSMA. Thus cecal abrasion is a reliable and reproducible method as a model for generation of intra-abdominal adhesions in mice which can be used to test therapeutic agents capable of blocking the fibrosis associated with adhesion formation. In addition, at the therapeutic doses of trametinib utilized, there was no impairment of the wound healing of the abdominal muscles and skin of the mice at the laparotomy site.

Effect of Trametinib on MMT

Figure 2:
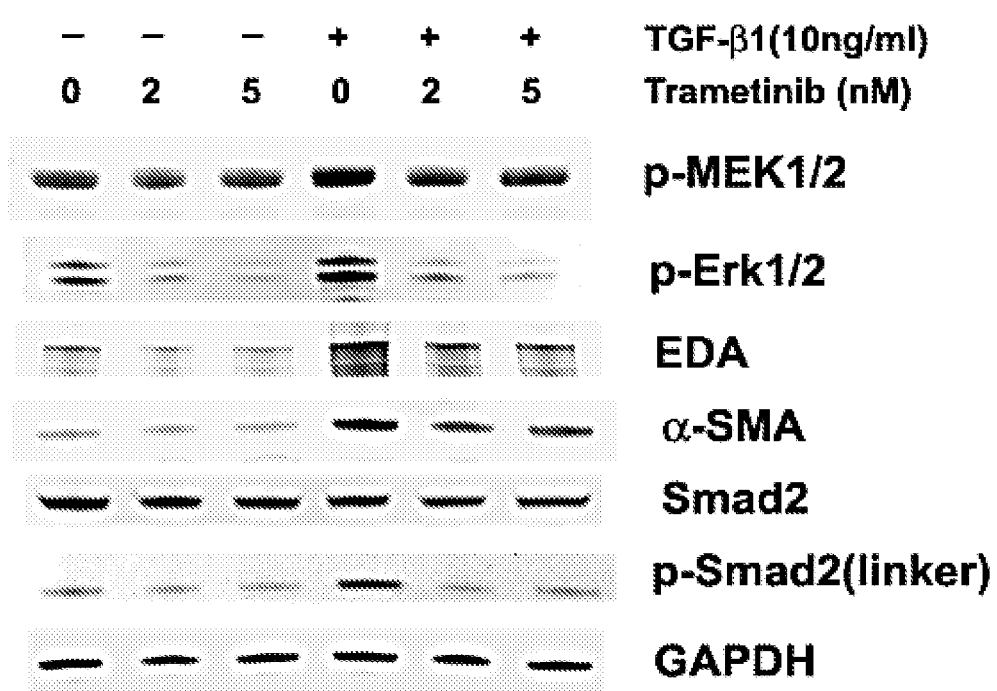
FIG. 2 Western analysis of proteins isolated from rat peritoneal mesothelial cells treated with and without TGF-β1 and with and without trametinib. Cells constitutively express phospho-MEK1/2 (the activated form of MEK1/2) with or without TGF-β stimulation whose expression is unaffected by trametinib. However, phospho-Erk1/2 shows a dramatic reduction after stimulation with TGF-β in the presence of either 2 or 5 nM trametinib as do $FN^{EDA}$, α-SMA and the phospho-Smad2(linker).

Isolated mesothelial cells were incubated under control conditions without either TGF-β or trametinib, with TGF-β or trametinib alone, or with both TGF-β and trametinib for five days (FIGS. 1 and 2). We have previously found that this length of time was required for maximal MMT effect of TGF-β on these rat cells [10]. As before, TGF-β produced a dramatic transitional effect, markedly altering the appearance of the cells, while trametinib alone had no effect and no apparent toxic effects with the cells maintaining a cobblestone appearance. Remarkably, trametinib blocked the effect of TGF-β and the cells retained their epithelioid morphologic characteristics.

Based upon our early observations (data not shown), TGF-β-treated cells gained αSMA and Col1a1 expression and we now show that such gains were prevented by trametinib. These insights led us to explore the potential mechanisms of action of trametinib using Western blotting analyses (FIG. 2). These experiments demonstrated that TGF-β produced a substantial increase in the phosphorylation/activation of Erk1/2 and phosphorylation of the Smad2 linker region as well as increases in expression of αSMA and FNEDA both of which agreed with our preliminary immunofluorescence studies alluded to above. These increases in gene expression of phosphor-Erk 1/2, FNEDA, αSMA and p-SMAD2 (linker) were blocked by as low a concentration of trametinib as 2 nM (FIG. 2).

Characterization of Adhesion Formation

Figure 3:
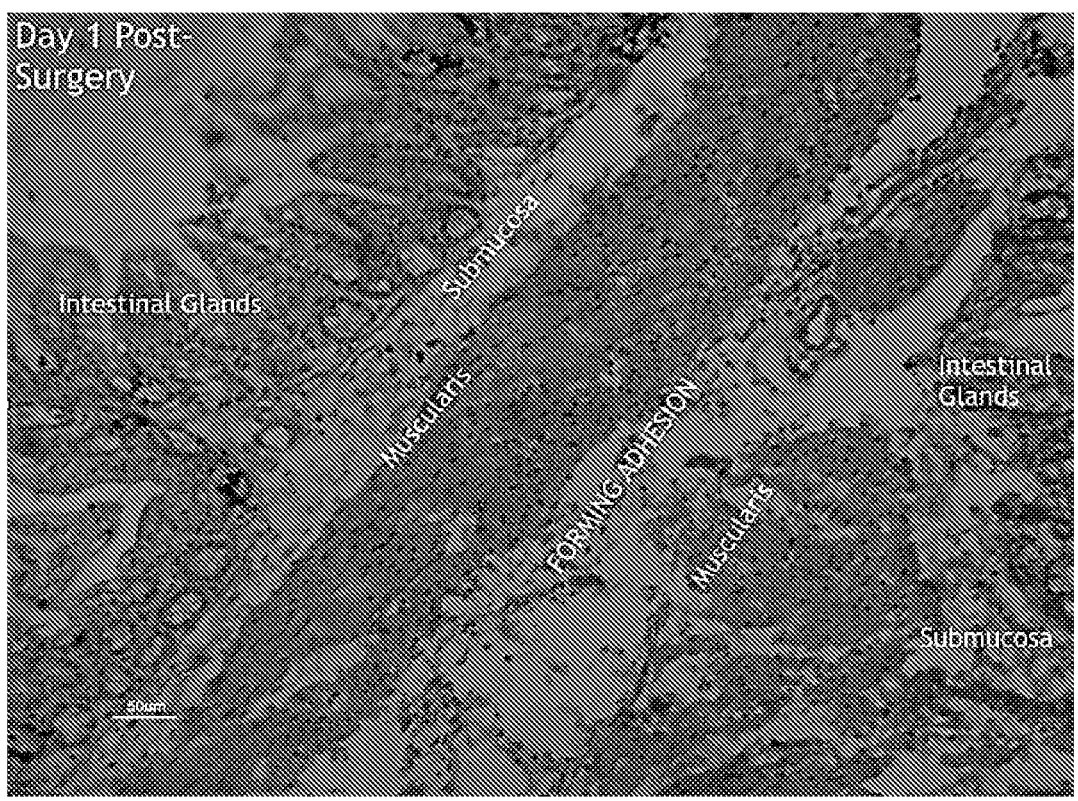
FIG. 3 Trichrome-section through adjacent intestinal loops showing a forming adhesion on day 1 post-surgery. The forming adhesion consists of a loose granular tissue with little organized structure.
Figure 4:
FIG. 4 Trichrome-stained section through adjacent intestinal loops showing a forming adhesion on day 2 post-surgery. The forming adhesion is becoming more cellular and well organized.
Figure 5:
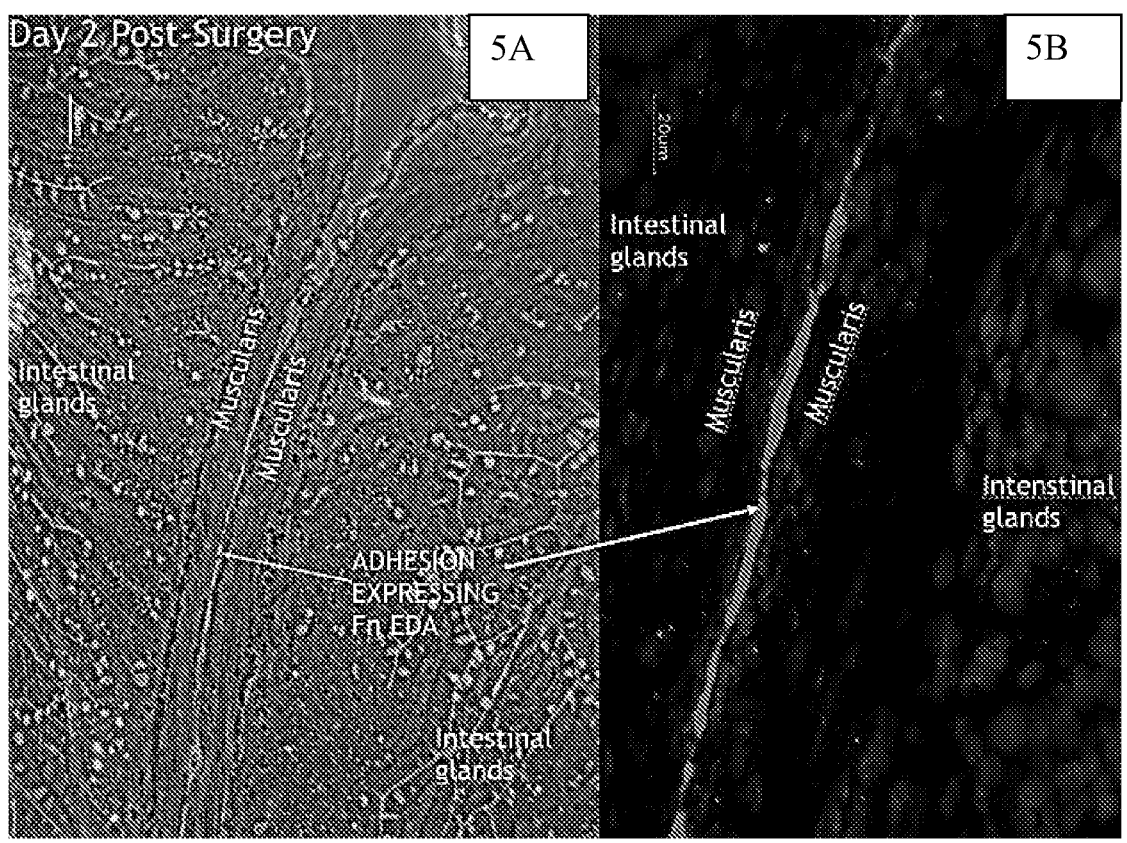
FIGS. 5A and 5B depict section through adjacent intestinal loops stained with an antibody to FNEDA showing a forming adhesion at day 2 post-surgery. A) Combined phase-immunofluorescent photograph showing the localization of the FNEDA antibody (arrows) within the forming adhesion. ×100; B) is a photograph within the same area as 5A but taken at a higher magnification ×400.
Figure 6:
FIG. 6 Trichrome—stained section through adjacent intestinal loops showing a forming adhesion on day 5 post-surgery. Highly cellular and well-formed adhesion with both arterial and venous structures.
Figure 7:
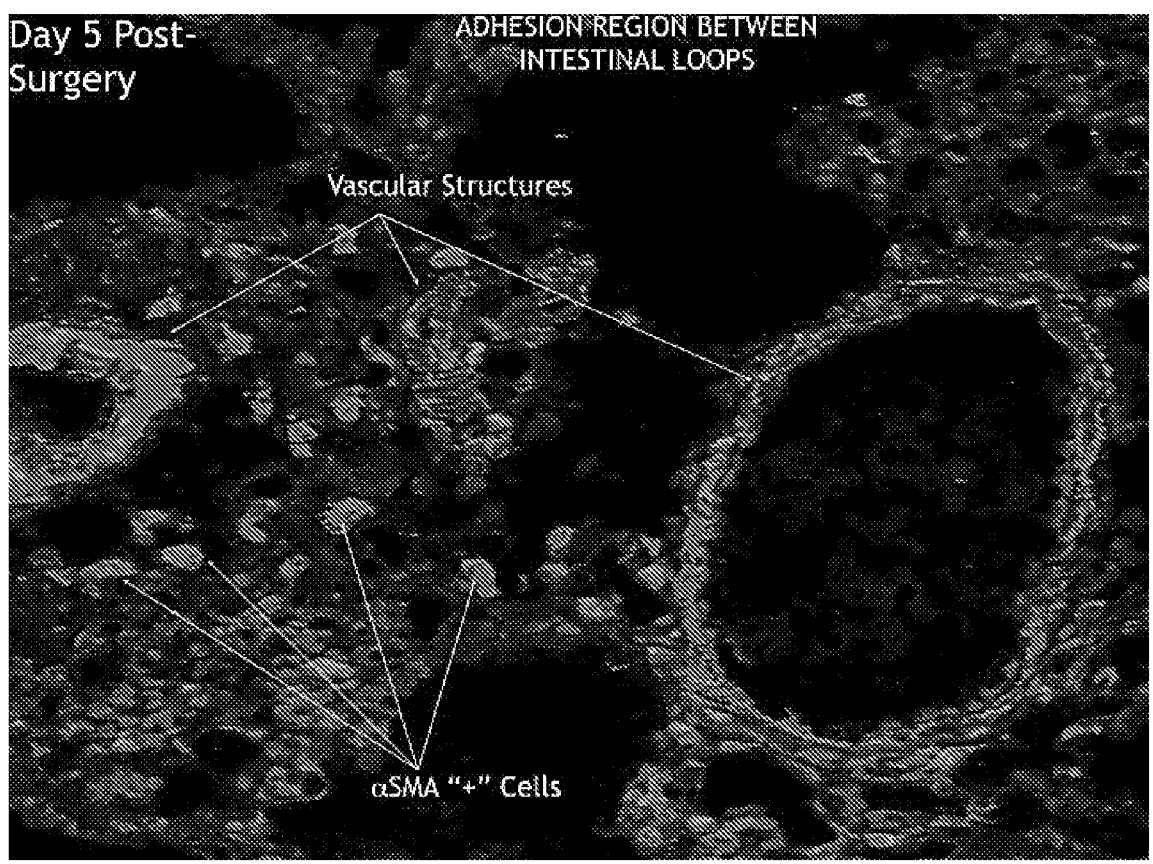
FIG. 7 Confocal immunofluorescent photograph showing localization of antibody to αSMA within a forming adhesion on day 5 post-surgery. (αSMA=red, DAPI=blue) Depicted is abundant localization of antibody to αSMA to cells within the adhesion indicating the presence of myofibroblasts within the adhesion. There is also localization of the antibody to the smooth muscle cells associated with the tunica media of blood vessels within the same area which serves as a "positive" control for the antibody ×400.
Figure 8:
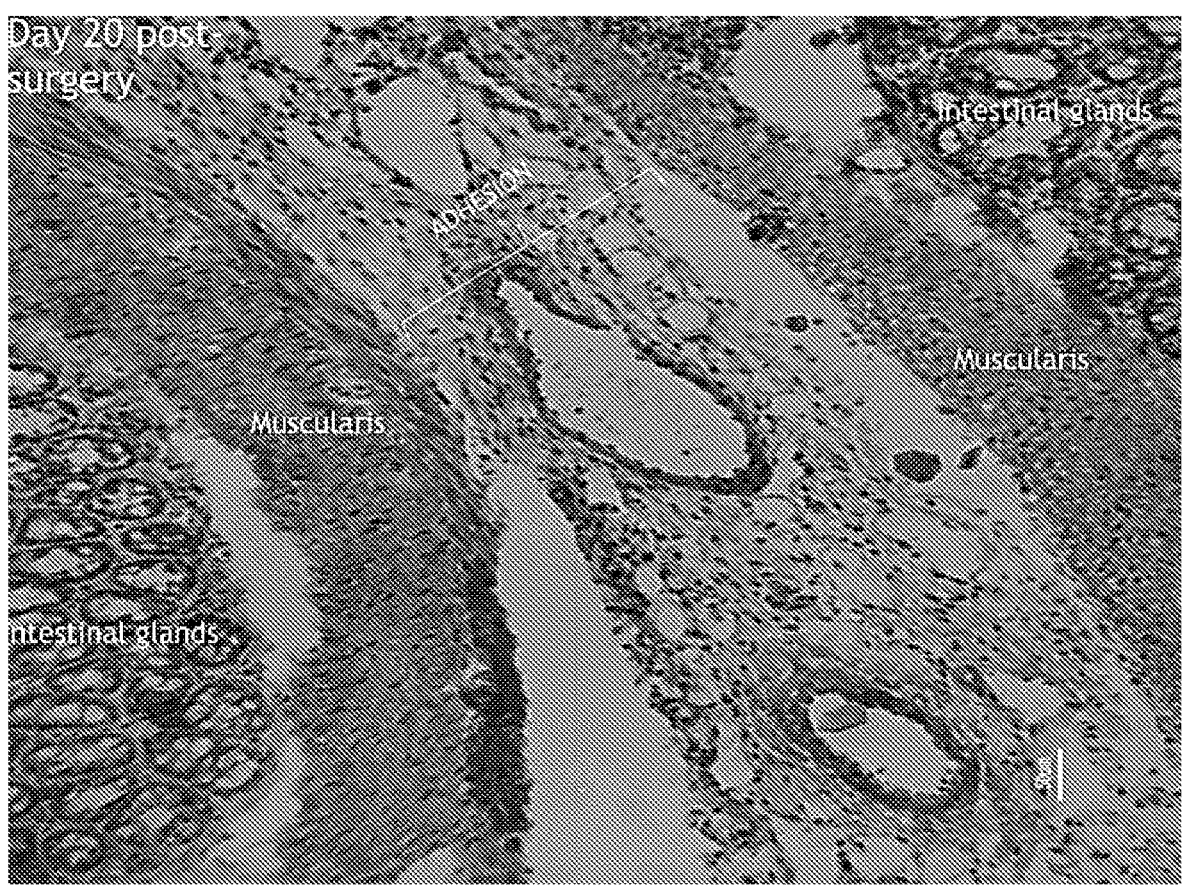
FIG. 8 details an adhesion day 20, post-surgery.

The histology of the large intestine of the mouse is similar to that of humans and consists of a lining of columnar epithelium containing many goblets cells. The epithelium is underlain by a lamina propria connective tissue layer, a submucosa and two layers of muscularis (an inner circular and an outer longitudinal layer) covered with a thin layer of mesothelium. After gentle abrasion of the cecum, the first appearance of adhesions was seen as early as day 1 post-surgery with the appearance of loose granulation tissue between adjacent intestinal loops (FIG. 3). The development of the adhesion proceeds during day 2 with greater cellularity within the developing adhesion (FIG. 4). In addition, there is the appearance of the FNEDA on day 2. FIG. 5a is a phase photograph which is merged with an immunofluorescent image and which is of the same region shown in FIG. 5b. The FNEDA localizes to the region between the adjacent intestinal loops. In both FIGS. 5a and 5b, there is a clear indication of FNEDA being present between the two adjacent loops of the mouse large intestine. Between day 2 and day 5 after surgery, the adhesion develops rapidly with greater cellularity as well as vascularization of the newly formed adhesion as shown in FIG. 6. The adhesion is a well-formed entity with many blood vessels including arterioles and venules and the presence of a collagen-containing ECM. Thus, the day 5 adhesions appear robust with well-formed blood vessels in an organized collagen-containing ECM. Interestingly, at day 5 post-surgery, cells which localize antibody to αSMA are present as shown in FIG. 7. In the same figure, the antibody to αSMA also localized extensively to the medial smooth muscle layer of several blood vessels whose staining serve as an internal control for antibody specificity. Adhesions which are present at days 8-23 post-surgery illustrate a continued maturation of the adhesions which become highly cellular and vascular (FIG. 8). As well, a mature ECM has formed with many blood vessels.

Trametinib Drug Treatment

Figure 9:
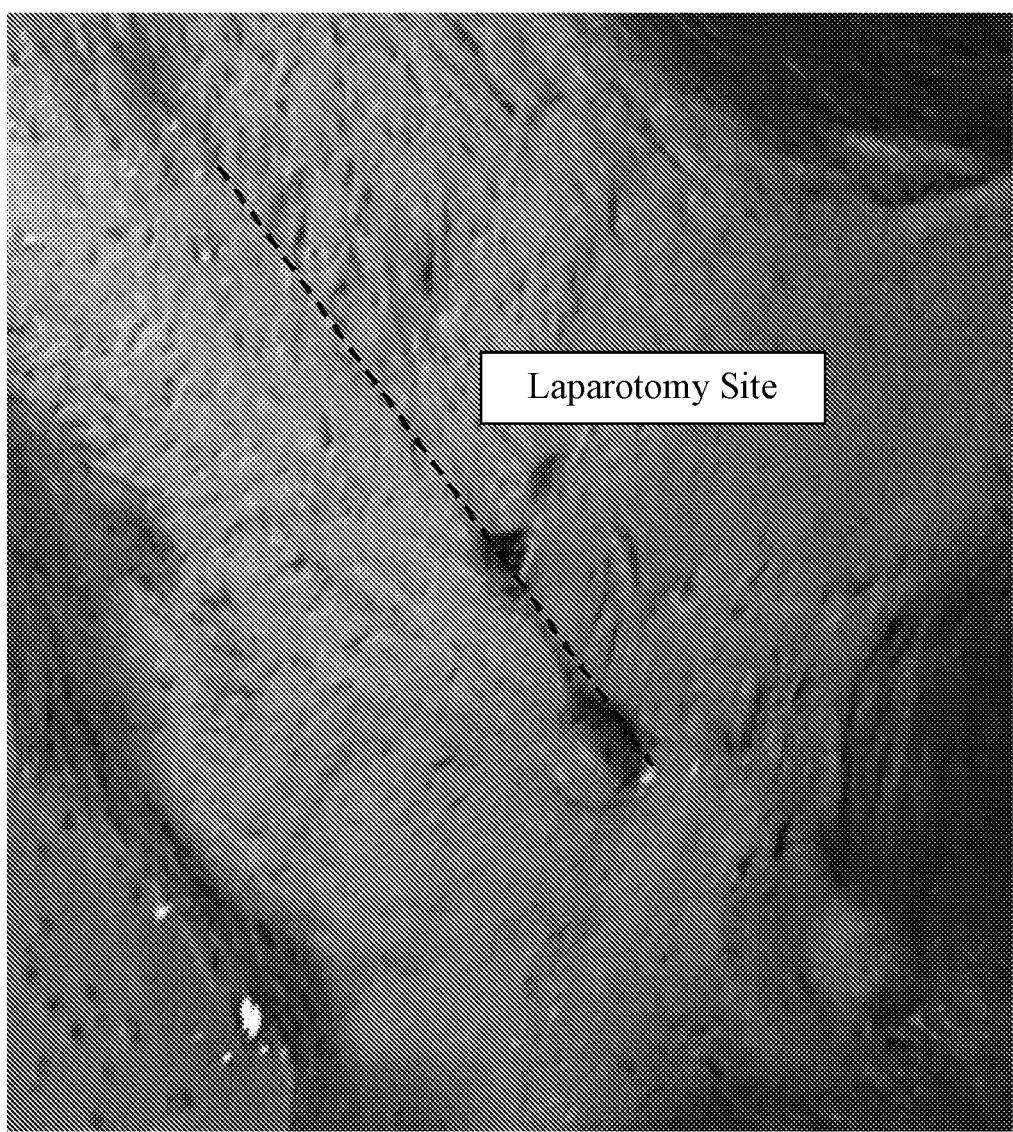
FIG. 9 Photograph of the abdomen of a mouse treated with the highest dose of trametinib. The laparotomy site has almost completely healed by 8 days post-surgery. In some animals, there is a complete closure of the incision by eight days.

Animals appeared to tolerate the drug with no adverse events noted. Changes in average weight within each group over the eight day period of drug delivery were unremarkable (1.0 mg dose: 2.2% average decrease in weight, 3.0 mg dose: 0.5% average increase in weight. As well, there appears to be no effect on wound closure and healing as shown in FIG. 9 which is representative of animals that received the highest drug dose (3 mg/kg/day). The drug is well-tolerated by the mice with no apparent toxicity noted. Since the drug is minimally soluble in water, dimethylsulfoxide (DMSO) was used as a "vehicle" to solubilize it. An additional series of 5 animals were subjected to the same surgeries as the previous mice, i.e., laparotomies and subdermal osmotic pump placement; however, the pumps contained no drug but did contain the drug solvent (DMSO). In these animals, adhesions formed in a fashion identical to control animals receiving no trametinib, demonstrating that DMSO had no effect.

Figure 10:
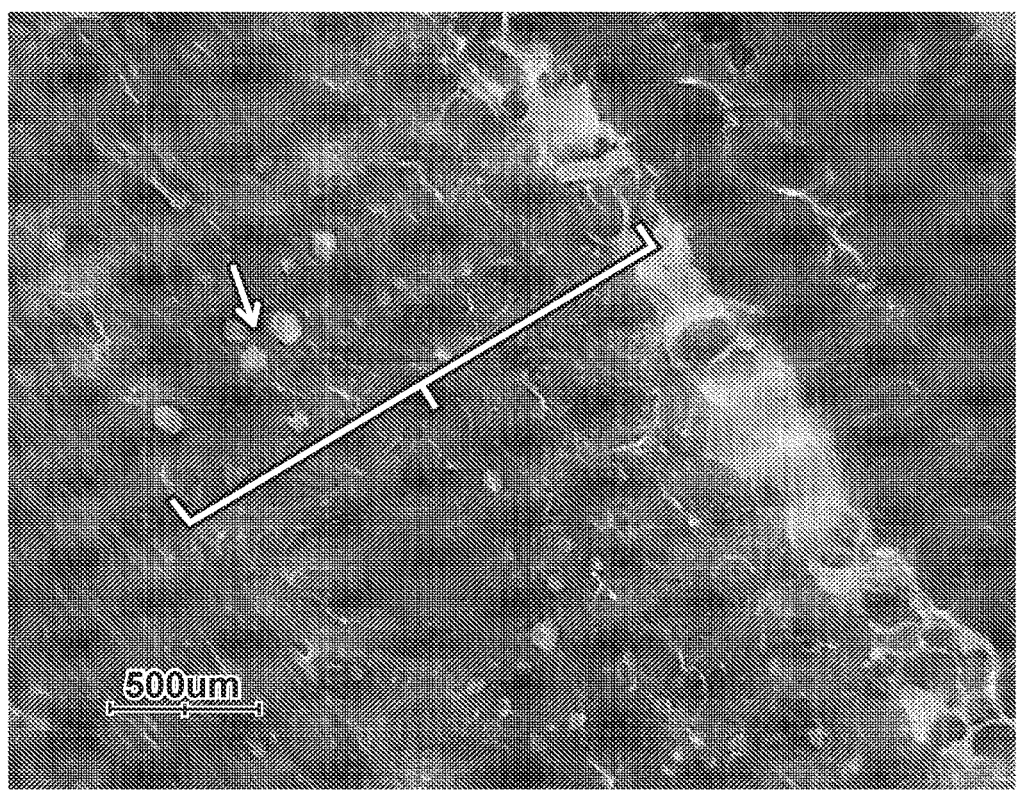
FIG. 10 Trichrome—stained section through adjacent intestinal loops showing a forming adhesion on day 8 post-surgery in mice treated with 0.1 mg/kg/day of trametinib. Animals treated with 0.1 mg of trametinib formed rare mature adhesions similar to those seen in control animals. Note the cellularity of the adhesion region as well as the presence of blood vessels (arrows) ×100.
Figure 11:
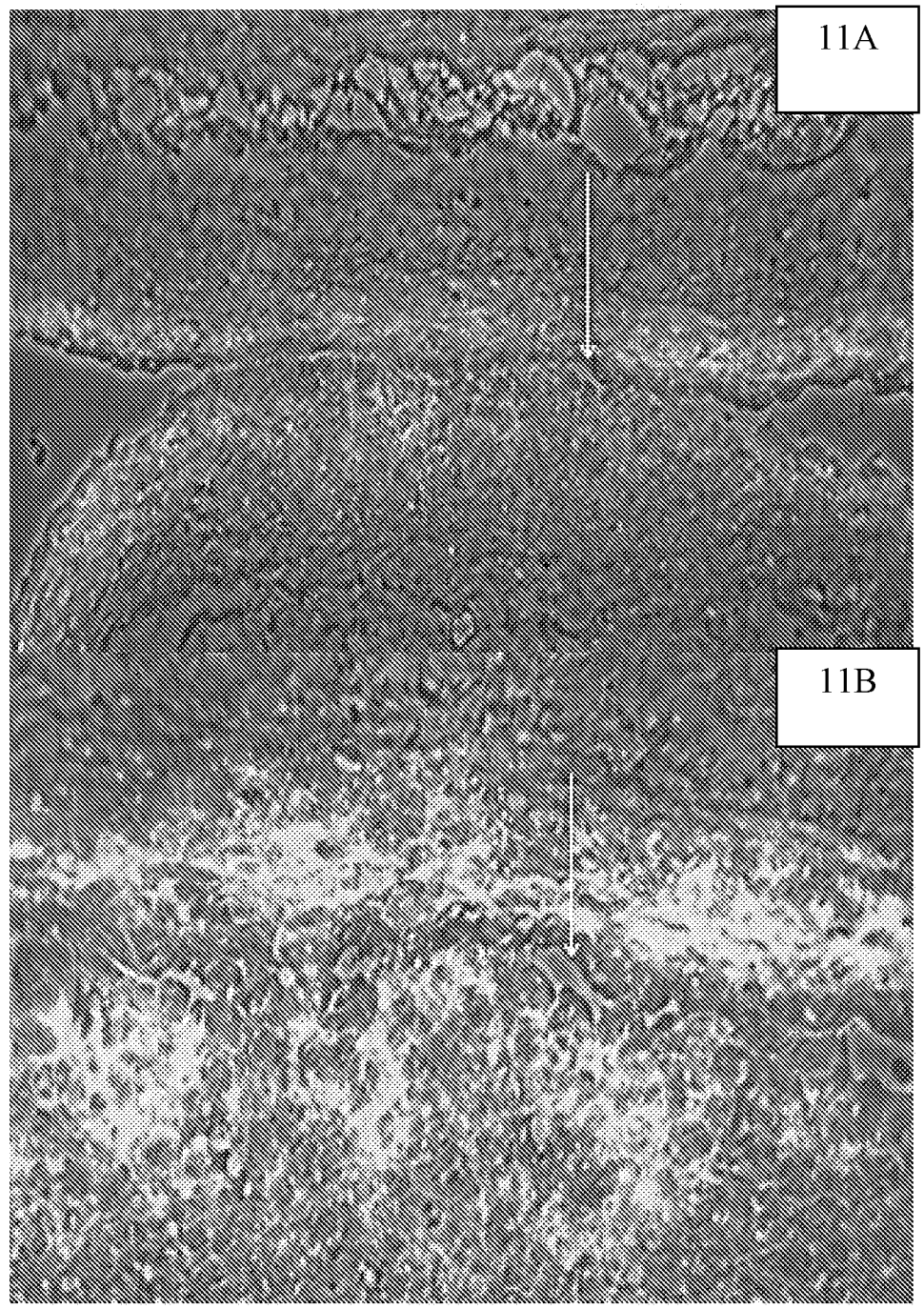
FIGS. 11 A and B. Combined phase-immunofluorescence photograph of a section through adjacent intestinal loop (IL)s. on day 8 post-surgery in mice treated with trametinib (0.1 mg/kg/day). FNEDA (green), αSMA (red), DAPI (blue). A) Although the intestinal loops are close to one another, there is clearly a defined "space" between the structures (arrows). Antibody to FNEDA (green) but not antibody to αSMA (red) localized to cells in the area immediately adjacent to the "space" between the adjacent intestinal loops. ×100. B) Photograph of the same area as shown in FIG. 11A but taken at a higher magnification showing extensive localization of FNEDA to cells adjacent to the opposed intestinal loops. ×250

In FIG. 10 is shown the intestine of a day 8 post-surgery mouse treated with trametinib (0.1 mg/kg/day). An adhesion has developed which is similar but less well-developed to that shown in FIG. 6 above. There are vascular structures present (arrows) and a weakly developed ECM containing collagen. FIGS. 11A and B shows an 8-day post-surgery adhesion from a mouse treated with 1.0 mg/kg/day. The white arrow indicates the site of the presumptive adhesion which is the empty space between the adjacent muscularis layers associated with the intestinal loops. These presumptive adhesion sites are difficult to identify and may represent areas containing fibrin as there are few if any cells associated within these regions.

Figure 12:
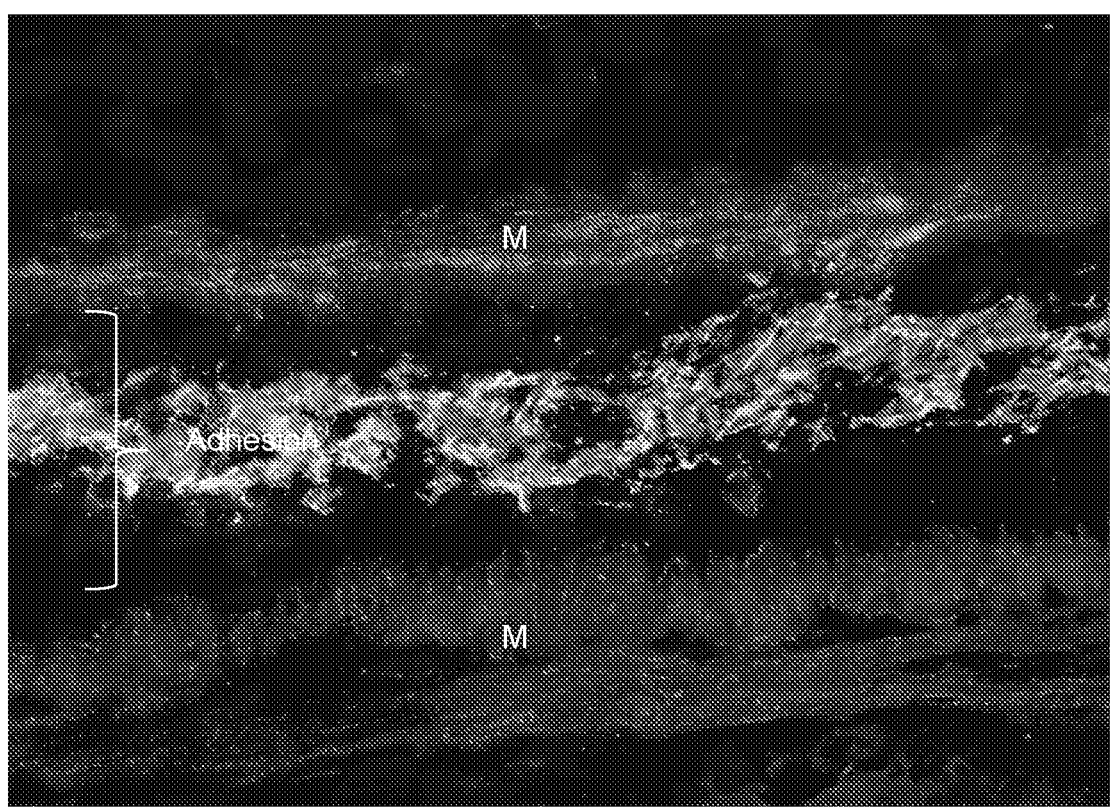
FIG. 12 Immunofluorescence photograph of a section through adjacent intestinal loops showing a forming adhesion in mice treated with 0.1 mg/kg/day of trametinib on day 8 post-surgery. FNEDA (green), αSMA (red), and DAPI nuclear stain (blue). Note that although the presumptive adhesion is highly cellular as demonstrated by the nuclear DAPI stain, there is little if any localization of αSMA in cells within the same area while there is considerable localization of FNEDA confirming the presence of proto-myofibroblasts (FNEDA+ and αSMA).
Figure 13:
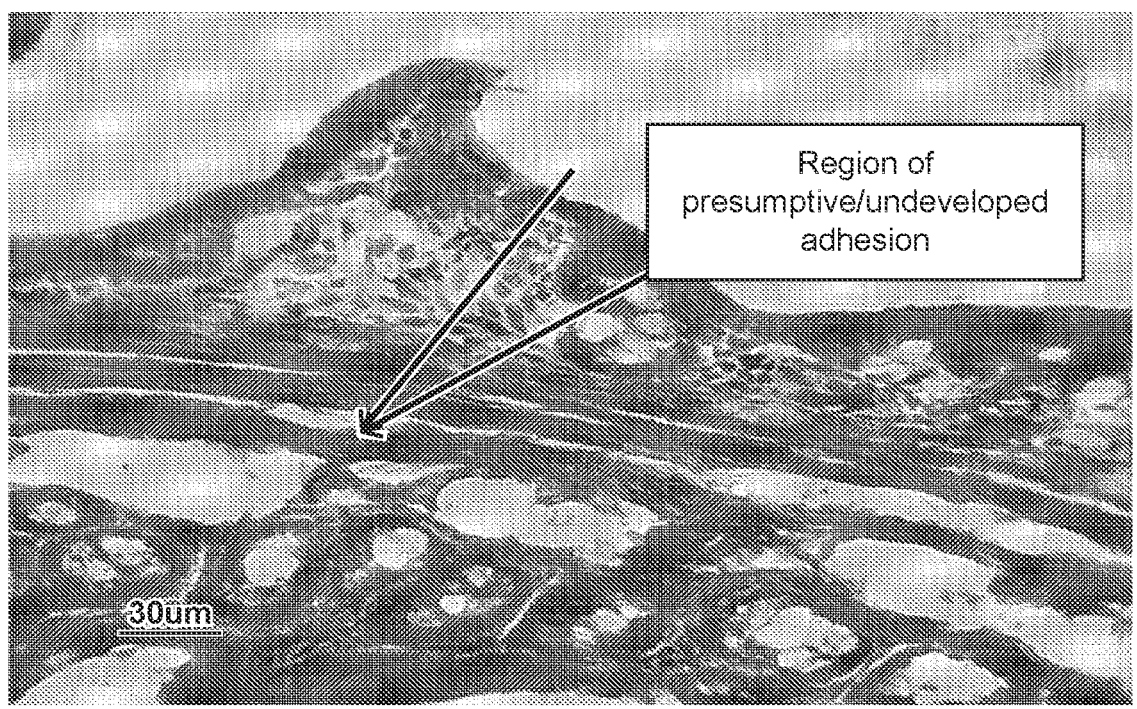
FIG. 13. Trichrome—stained section through adjacent intestinal loops showing a forming adhesion on day 8 post-surgery in mice treated with 3 mg/kg/day of trametinib. Mice treated with the highest dose of trametinib (3.0 mg/kg/day) did not form adhesions. There are many regions where the intestinal loops with intact epithelium and muscularis layers (M) are close together, but which neither develop the granular tissue shown in untreated controls nor show evidence of the presence of myofibroblasts by immunohistochemistry ×100.
Figure 14:
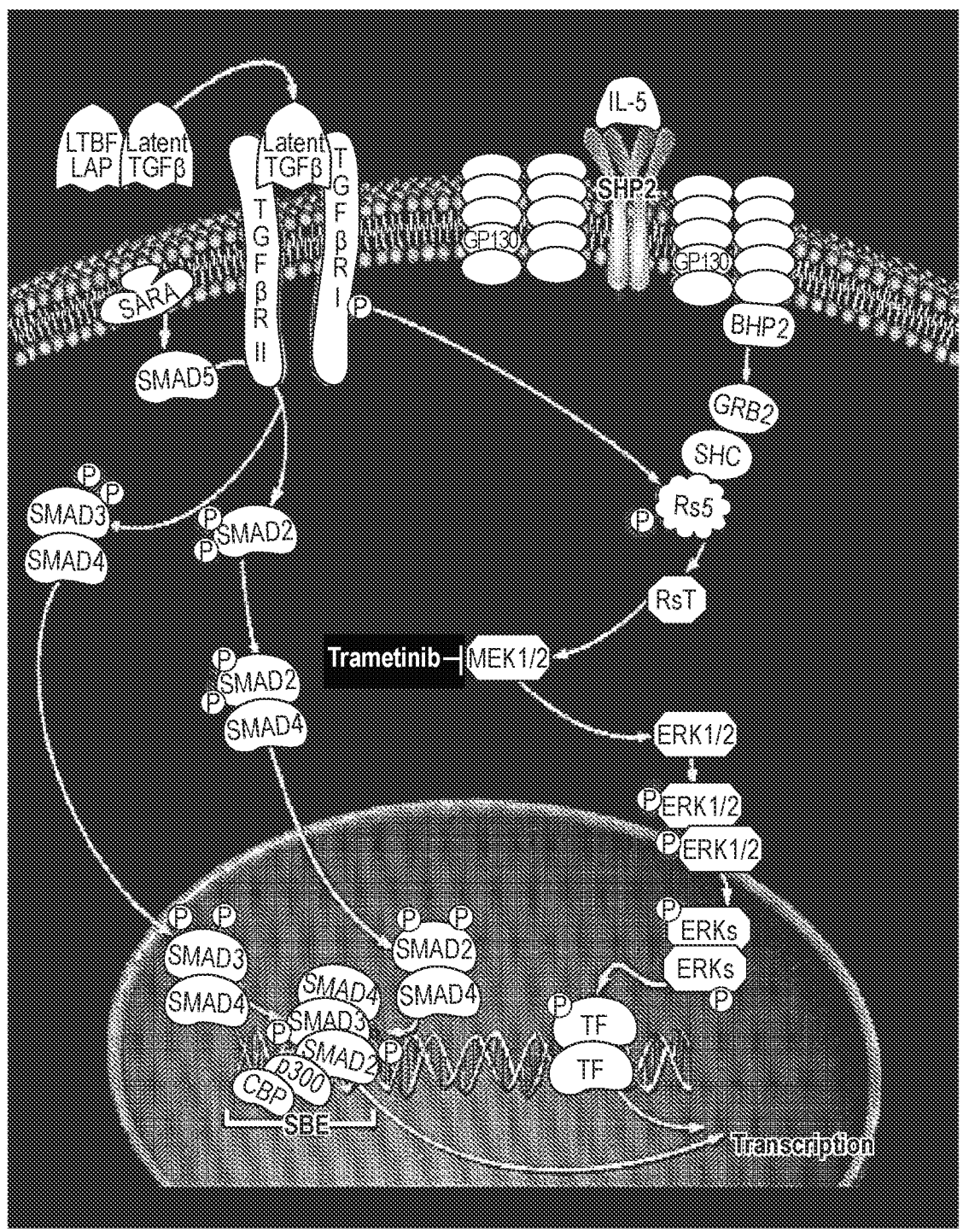
FIG. 14. TGF-β and IL-6 pathways leading to activation of MEK1/2 and Erk1/2 and their inhibition by trametinib. Both TGF-β and IL-6 have been shown to activate a "downstream" common signaling pathway through Ras, which results in the activation of Erk1/2. Erk1/2 have many potential downstream activities but only their role(s) as transcriptions factors is illustrated. The relevant pathways have been simplified for clarity, but the figure shows the most important elements in the present context. Abbreviations: LAP Latency Associated Peptide, SMAD, Sma and Mad related family of signal transducers, LTBP, Latent Trapp Binding Protein, GP130, Glycoprotein 130, IL-6, InterLeukin 6, SHP2, tyrosine phosphatase, GRB2, Growth Factor Receptor-Bound protein 2 SHC, SHC adaptor protein, Ras, Ras family called small GTPase Rat proto-oncogene serine/threonine-protein kinase, MEK, MAPK/ERK Kinase, SARA, Smad Anchor for Receptor Activation, ERK, extracellular signal regulated kinase, P300, transcriptional co-activating protein, CBP, Creb Binding Protein, TF, Transcription Factor, SHE, Smad Binding Element.

FIG. 12 shows an 8-day post-surgery adhesion from an animal treated with a dose of trametinib (0.1 mg/kg/day) which has been stained with antibodies to αSMA (red) and $FN^{EDA}$ (green). This immunofluorescent image shows a formed adhesion between the intestinal loops; however, note that the FNEDA antibody localizes within the presumptive adhesion region while the αSMA (red), a "biomarker" for myofibroblasts, is absent suggesting there are none in this same region. Note also that muscularis (M) in both intestinal loops does localize the αSMA antibody which serves as a positive control for antibody specificity.

Discussion

Peritoneal adhesions, which are most commonly caused by abdominal surgical procedures, are a leading cause of surgical morbidities [14, 15]. However, whether caused by obstruction, ischemia, inflammatory bowel disease or surgical injury, it is highly likely that a limited number of cellular and molecular mechanisms are responsible for the formation of the scar tissue comprising the adhesion, irrespective of the cause. The critical cell in this process is the activated fibroblast or myofibroblast which produces increased amounts of fibrillar collagens as well as other ECM components and which expresses αSMA and FNEDA, molecular markers of activated myofibroblasts [14]. The accumulation of myofibroblasts and the uncontrolled persistence of their elevated biosynthetic functions are crucial determinants of the extent and rate of progression of fibrotic reactions and of their clinical course, prognosis, and response to therapy.

The origins of myofibroblasts may differ depending on the affected organ and the initiating event, but there are several important potential sources: (i) Activation of tissue resident fibroblasts in response to specific signals from infiltrating inflammatory cells [15]; (ii) Recruitment of bone marrow precursor cells known as fibrocytes which express bone marrow cellular surface markers such as CD34, but are capable of extracellular matrix (ECM) production [15,16]; and (iii) Trans-differentiation of epithelial, mesothelial, and endothelial cells into activated myofibroblasts. Although this process was originally described in epithelial cells and designated epithelial to mesenchymal transition (EMT), it is now known that very similar processes occur in the case of mesothelial (MMT) and endothelial (EndoMT) cells [17-19].

In these transitions, the epithelial, mesothelial or endothelial cells may lose their specific markers and traits, such as expression of E-cadherin, and acquire a mesenchymal or myofibroblast phenotype initiating expression of αSMA, vimentin and ECM proteins including the FNEDA. One of the hallmarks of the ECM associated with fibrotic diseases is the presence of a contractile myofibroblast. It is currently well-recognized that, regardless of its origin, the resident myofibroblasts in a fibrotic lesion must have the cellular protein components to permit force generation. A requirement of this competency is, firstly, the expression of FNEDA. When this occurs, the presumptive myofibroblast is termed a "proto-myofibroblast. It is only later after the proto-myofibroblast expresses αSMA that it is termed a myofibroblast. Without the expression of both these proteins, it not possible for the myofibroblast to transfer force from the interaction of actin and myosin located inside the cell across the cell membrane to the ECM. The fact that the cells in the adhesion shown in FIGS. 11A and B expresses only FNEDA and not αSMA (compare FIGS. 11 and 7) suggests that the drug has blocked the conversion of the precursor fibroblast into a functional myofibroblast since both αSMA and FNEDA are required to mediate the transfer of intracellular force to the ECM [20]. However, this observation has been quite rare in our studies. Firstly, the occurrence of even presumptive adhesions in the drug-treated animals is a rare event. Entire large intestine bowel from 3 mice for each dose of trametinib were serially sectioned and searched for regions where the intestinal loops were bound to one another. Secondly, when such regions were found, they usually were not developed and were lacking in cellularity. Thus, the rare adhesions which were found were very modest in terms of their molecular composition of biomarkers (αSMA and FNEDA) as compared to those found in untreated animals. No adhesions were found in animals receiving the highest dose.

Theoretically, MMT may be an important cellular mechanism for abdominal adhesions, acting as a source of myofibroblasts. While the origin of the myofibroblasts found in adhesions remains a contentious issue [21], in the present study, we sought to validate our previous findings that the MMT elicited by TGF-β could be blocked by a MEK1/2 inhibitor, already in clinical usage for other purposes.

Therefore, the results demonstrate that trametinib, a drug presently being used in the treatment of malignant melanoma, was very effective in blocking MMT of rat peritoneal mesothelial cells. This was observed at both the morphological level in which the characteristic cobblestone appearance was maintained (FIG. 2) and at the molecular level in which the expression of FNEDA and αSMA were inhibited and the phosphorylation of Erk1/2 was essentially blocked completely (FIG. 2). Importantly however, it should be noted, that the concentrations of trametinib used in the present experiments were considerably lower (2 or 5 nM) than that used in experiments involving cultured melanoma cells (100 nM). This suggests that a positive therapeutic response with trametinib could be attained at a much lower dose for treatment and prevention of fibrotic reactions than that required for tumor responses in vivo, minimizing any potential toxic events.

Indeed, this finding of such a low dose is surprising for these cultured melanoma cells. In prior studies for tumor response, the required dose was at least 20× if not 50× the dose required in our applications. Accordingly, the possibility of the therapeutic range being below that for the cultured melanoma cells, provides for a highly useful therapeutic option at otherwise far below therapeutic levels for tumor responses. Administration of low doses may provide a better safety profile as the occurrence of side effects can be limited based on the low dose form to be administered. Furthermore, no prior studies would have suggested that such a low dose form would be therapeutic or be useful, even in cultured cell studies.

In the present adhesion model, we found that there was a dramatic increase in production of extracellular matrix containing collagen and FNEDA, and in which αSMA-tagged myofibroblasts were embedded. Significantly there was a rapid formation of blood vessels within the adhesion suggesting hypoxic conditions. Based upon a large body of knowledge in many systems, it is known that TGF-β is primarily responsible for much of the untoward fibrotic response. Significantly, elevated TGF-β1 levels have been found in the peritoneal fluid of patients during/after abdominal surgery whose levels correlated with the severity of abdominal adhesion formation. The complex signaling pathways activated by TGF-β involve both canonical and non-canonical pathways. In the present context, the critical downstream event elicited by non-canonical signaling is the activation of Erk1/2 by MEK.

The present findings demonstrate that trametinib can effectively inhibit the formation of adhesions in a mouse model that reflects potential clinical situations. Since therapeutic approaches to adhesion formation are extremely limited, the clinical testing of trametinib appears to be warranted. This is particularly true since the effective dosage to inhibit the fibrotic process is much lower than that required in the cancer therapeutic situation. Importantly, our observations also demonstrate that the effective dosage of trametinib had no adverse effect on the healing of the surgical wound required to access the abdominal cavity in the model.

Trametinib is typically prescribed at a 1-2 mg dose, once daily. Frequently it is co-administered with a second compound, Dabrafenib, which is taken at much higher dose rates. The studies herein neither require the co-administration protocol with Dabrafenib, nor the concentrations of trametinib as required for cancer treatments.

The trametinib therapeutic therefore may be administered according to the methods as described herein. For example, before a surgical procedure, at least one dose of trametinib can be provided to a patient prior to surgery, wherein the dose is between about 0.01 mg to about 2.0 mg, administering at least one further dose of trametinib at the same or reduced concentration on a daily basis until the risk of abdominal adhesion has passed. In certain embodiments, the dose is between 0.01 to about 2.0 mg to a patient. In preferred embodiments, the range is between 0.01 mg to about 1.5 mg, or to about 1.0, 0.75, 0.5, or 0.25 mg, inclusive of all numbers, whether explicitly stated or now. Or, the trametinib can be given at a dose of between 0.001-0.025 mg/kg body weight.

A method of reducing the occurrence of abdominal adhesions in a patient undergoing a surgical procedure comprising administering to said patient at least a first dose of trametinib between 0.01 mg to 2.0 mg, and after said surgical procedure, administering to said patient a further dose of trametinib between 0.01 mg to 2.0 mg, daily, for at least seven days post-surgery.

A method of reducing the severity of abdominal adhesion due to surgical complications comprising: administering to said patient at least a first dose of trametinib between 0.01 mg to 2.0 mg, and after said surgical procedure, administering to said patient a further dose of trametinib between 0.01 mg to 2.0 mg, daily, for at least seven days post-surgery. Preferably, the dose is provide between 0.01 mg to 2.0 as an initial dose and a lower dose of between 0.01 mg to 1.0 mg, is provided daily for at least seven days post-surgery.

A method of reducing the severity of abdominal adhesion after a surgical procedure comprising: administering to said patient at least a first dose of trametinib between 0.01 mg to 1.0 mg, daily, and thereafter continuing for at least seven days post-surgery.

A method of prevention of the formation of abdominal adhesion prior to a surgical abdominal procedure comprising: administering to a patient undergoing said surgical abdominal procedure a first does of trametinib at a dose of between 0.001 mg/kg body weight and 0.025 mg/kb body weight; and provide at least a second dose at the same or reduced level to the first dose after the surgical procedure. In certain preferred embodiments, prior to surgery, several doses of trametinib are provided to generate a sufficient concentration of the therapeutic in the body.

A particular benefit of this therapeutic and the methods described herein is that wound healing is not impacted by these methods. A primary concern for treatment would be that internal wounds would not heal after a surgical procedure. However, based on the studies performed to date, we have not identified any impact on the rate and efficacy of wound healing.

Treatment and administration of the therapeutic may include systemic applications and direct to tissue applications.

Study Highlights: We know that post-surgical adhesion are common (>90% of patients will develop adhesions after abdominal surgery) and that the formation of these adhesions is extremely costly (>1.5 billion/year) and cause great morbidity (pelvic pain, bowel obstruction and infertility) with currently no good therapeutic remedies (a study showed 18% of hospital admissions were secondary to abdominal adhesions). Accordingly, treatments for some of all of these patients, to prevent or treat adhesion formation is a critical unmet need.

We describe herein the validation of an animal model which can be used to test drugs effective in blocking pathways regulating ECM deposition associated with adhesion formation. In addition to the trametinib drug that is identified herein, the model can be utilized to identify drugs with the potential to block the formation and progression of intestinal adhesions as well as fibrosis which occurs in other organs and tissues such as the lung, heart, kidney, liver, bladder and skin.

The pharmacokinetics of the therapeutic trametinib are such that they are effective in a patient at a particular concentration. Based on the half-life of the therapeutic in the body, it is possible to provide such therapeutic levels through a first initial dose at a first concentration and at least a subsequent dose at a second, lower, concentration. Thereby, the first dose loads the patient to meet a threshold concentration, and the second dose maintains the concentration in the body at therapeutic levels for the duration of the need for treatment, typically less than 10 days post-surgical procedure.

The methods, however, may also include treatments for other adhesions. For example pelvic adhesions, heart adhesions, intestinal adhesion, reproductive adhesions of the vagina or uterus, pericardial adhesions, among others, are also treated by the therapeutic methods described herein. Indeed, a critical fibrotic disease is that of pulmonary fibrosis.

The underlying mechanism responsible for pulmonary fibrosis is likely analogous to that which occurs during abdominal adhesions formation, wherein the development of each follows similar activation by several cytokines and growth factors including the TGF-β family. While the formation of abdominal adhesions can be usually pointed towards surgical procedures, the formation of pulmonary fibrosis is typically formed from occupational or environmental concerns, including those who have worked with or around asbestos, silicates, coal miners, ship workers, and the like. Additionally, those who inhale dust contaminated with bacteria, fungal, animal products, dander, and such are frequently susceptible to formation. Finally, smoking can both exacerbate and also lead to the initial formation of the disease. In addition, in idiopathic pulmonary fibrosis, there is no known agent responsible for the progressive changes in lung structure clinically associated with the pathophysiology of this disease. Idiopathic pulmonary fibrosis is a devastating, age-related lung disease of unknown cause that has few treatment options. Although chronic inflammation was initially thought to be the cause, current evidence suggests that the disease process is driven by the same pathophysiologic mechanisms underlying other fibrotic diseases, i.e., the generation of myofibroblasts from damaged alveolar epithelium and/or other sources as well.

We evaluated the efficacy of treatment of pulmonary fibrosis based upon our understanding of the mechanism and efficacy found in abdominal adhesions.

Figure 15A:
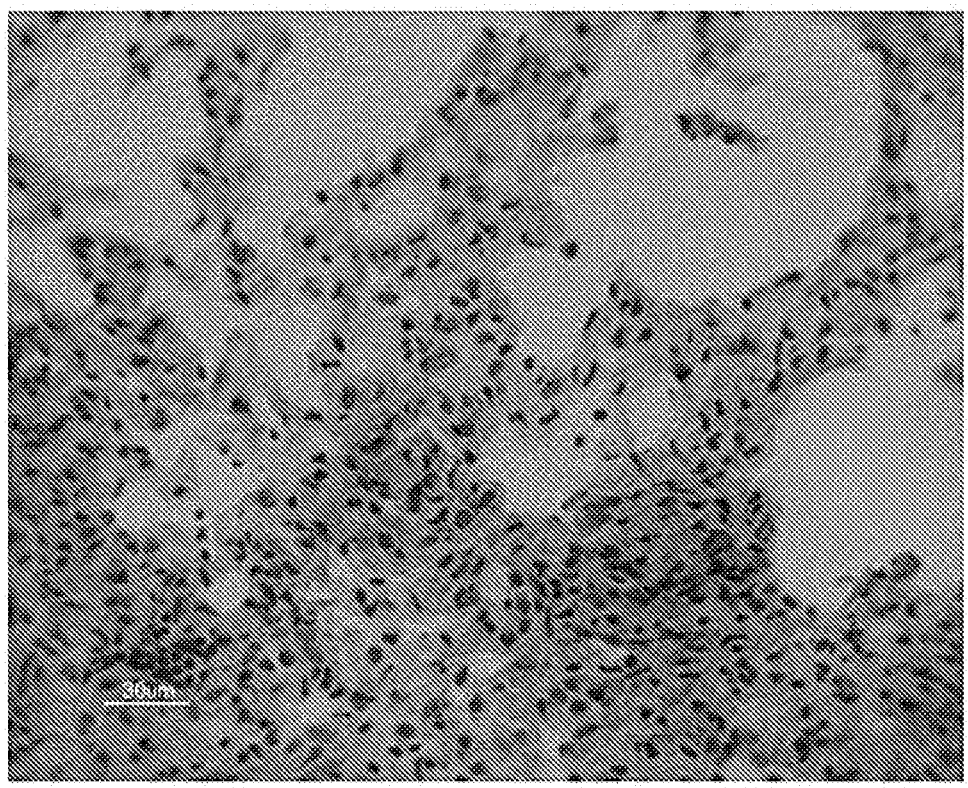
FIGS. 15 A and B depict lung tissues, wherein 15A depicts bleomycin impacted lung tissues with a carrier, identifying extensive fibrosis formation and 15B depicts lungs treated with a 3 mg/kg solution of trametinib, having lack of prominent fibrosis and the presence of lacy air spaces indicating normal lung tissues.
Figure 15B:
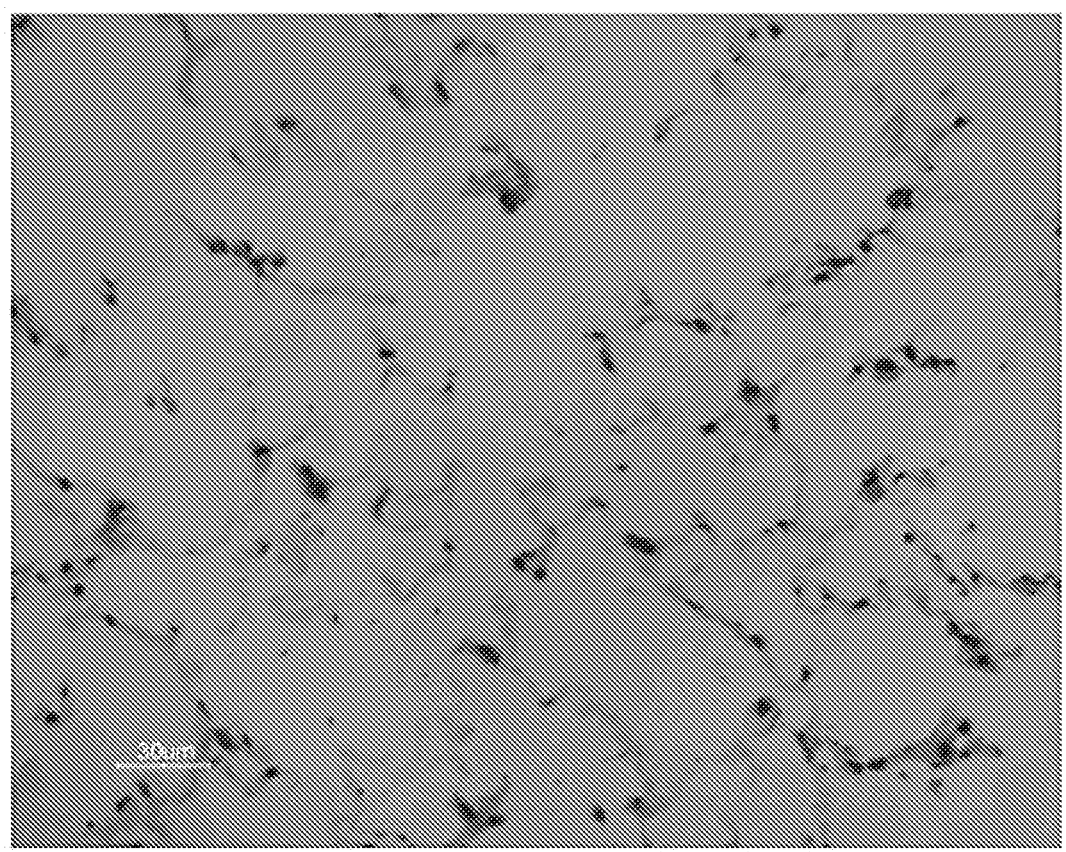

FIGS. 15A and 15B depict lung tissues from a two different studies. In each case, a mouse was instilled with 50 µg of bleomycin dissolved in normal saline (100 µl). After one week, an osmotic pump, releasing 6 µl/day of vehicle, or vehicle and drug was placed subcutaneously between the scapulae of the mouse. After ten days, the mice were sacrificed and tissues stained with trichrome.

FIG. 15A depicts a mouse lung treated with only vehicle or dimethyl sulfoxide. The tissue shows thickened alveolar walls, enlarged air spaces, a grossly distorted lung structure (specifically, a lack of "lacy" air spaces" and extensive fibrosis formation throughout. By contrast, FIG. 15B depicts lung from a mouse treated with a solution of 3 mg/kg of trametinib dissolved in the dimethyl sulfoxide. In comparison to FIG. 15A, the tissue of FIG. 15B has a more normal appearance of the lung tissue, the presence of "lacy" air spaces, and lacks prominent fibrosis.

Indeed, the trametinib dose, after the damage from the bleomycin to the lung tissue, resulted in a dramatic reduction and prevention of further fibrosis formation in the lung tissue.

Figure 16A:
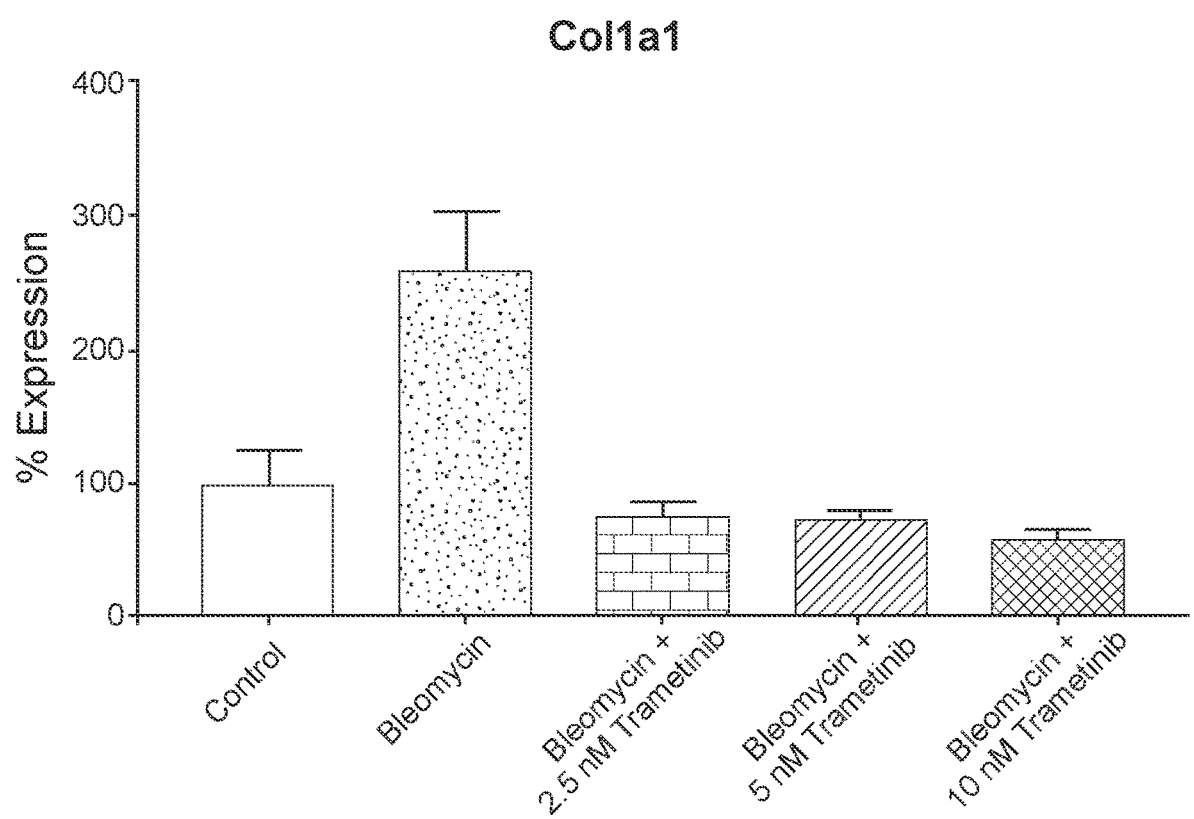
FIGS. 16 A, B, and C depict three graphs depicting Type I collagen, fibronectin EDA (FNEDA), and an αSMA smooth muscle actin tested against a control, bleomycin, and three different doses of trametinib.
Figure 16B:
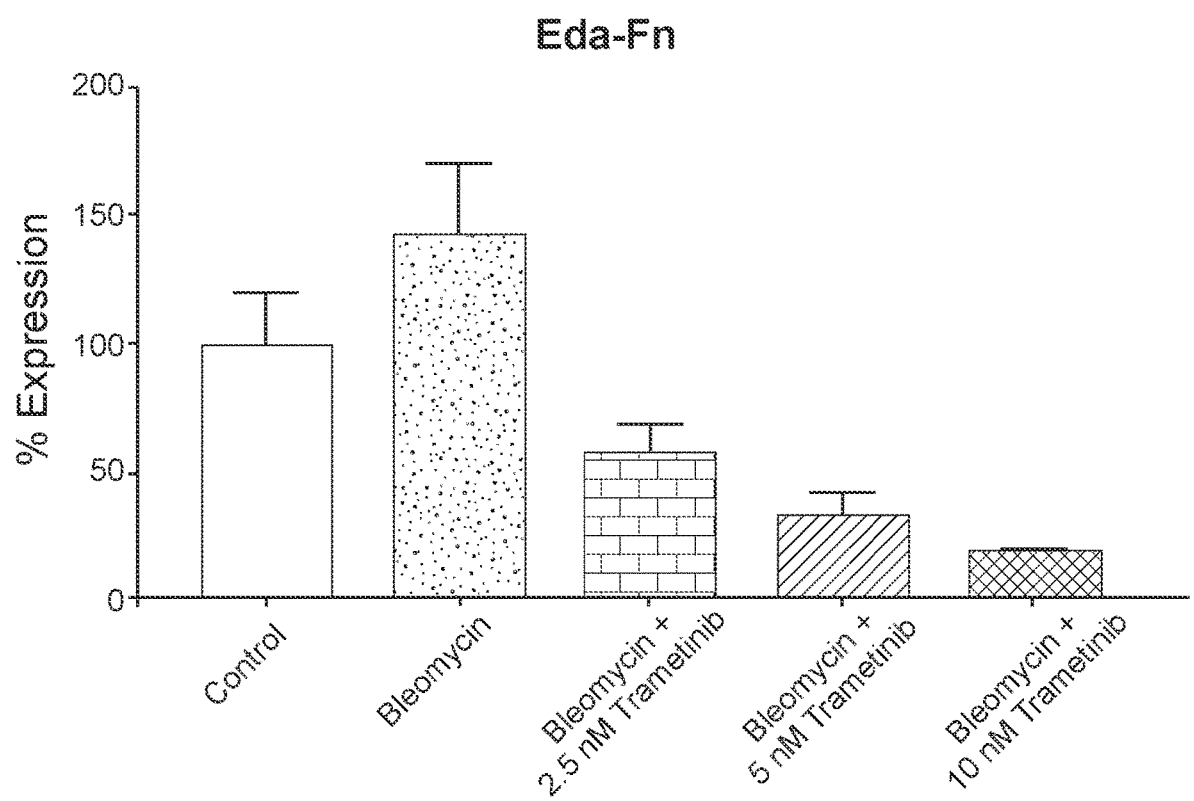
Figure 16C:
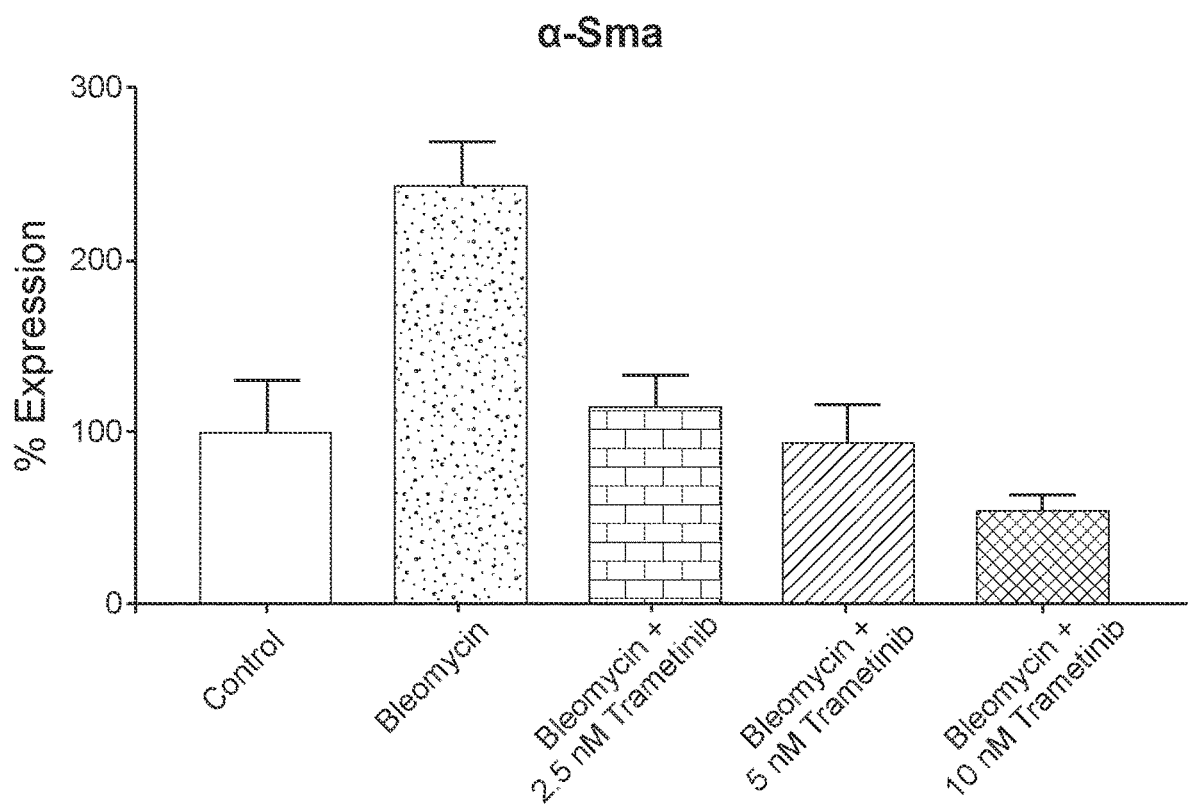

FIGS. 16A, B, and C further evaluate the ability of trametinib to control lung fibroblases isolated from mouse lung tissue. The three graphs represent expression of several pro-fibrotic genes (type I collagen and FNEDA) and αSMA. Fibroblasts isolated from mouse lungs were placed in cell culture and treated either with saline (control) or bleomycin dissolved in saline and 3 different concentrations of trametinib (2.5, 5 and 10 nano molar) dissolved in DMSO. After treatment with the drug, RNA was extracted and quantified by qPCR. mRNAs for type I collagen (Col1a1), e FNEDA and αSMA are shown. Control values in FIGS. 16 A, B, and C were set to 100%.

As is evident, expression of mRNA for each of the pro-fibrotic genes is dramatically increased for lung fibroblasts treated in vitro with bleomycin as compared to control cells treated with vehicle alone. For Col1a1 and αSMAa, an increase in expression of more than 200% is provided, with an increase of nearly 150% for FNEDA. By comparison, expression of these same pro-fibrotic genes in bleomycin-treated lung fibroblasts given 2.5 nM, 5 nM, or 10 nM of trametinib led to either similar results as to control, i.e. even with the bleomycin, damage either did not accrue, or there was a significant reduction in expression of the pro-fibrotic genes.

The presence of myofibroblasts expressing FNEDA and αSMA are accepted biomarkers of the fibrotic process. Since treatment of animals with the MEK 1/2 inhibitor trametinib resulted in a significant reduction in expression of these pro-fibrotic biomarkers, these studies indicate that trametinib has therapeutic potential that can be used to block or ameliorate fibrosis not only in the abdominal cavity after surgery but also in the lung and potentially other organs and/or tissues.

Accordingly, a proposed method for treatment of pulmonary fibrosis comprises administering to a patient at risk for developing pulmonary fibrosis an effective amount of trametinib, wherein the level of trametinib is provided at a level between 0.001 mg/kg body weight and 0.025 mg/kg body weight. In certain preferred embodiments, said level of trametinib is provide at between 0.01 mg to 2.0 mg a day.

Further embodiments using the above therapeutic levels are provided to treat a patient suffering from pulmonary fibrosis, wherein the administration of trametinib is sufficient to reduce the formation of adhesions or to prevent or retard the progression of the disease. Preferred embodiments may utilize and aerosol to provide pharmaceutical compositions directly to the lungs.

In certain preferred methods, we can also evaluate the presence of absence of myofibroblasts in a patient by evaluating or detecting the presence of FNEDA or αSMA, or both. Preferably, these markers are detected by measuring the presence in a biopsy taken from the patient. In certain cases, it may be possible to measure FNEDA in plasma whose levels may correlate with disease severity. As well, there are fragments of collagen which may also correlate with disease severity which can also be measured in plasma or urine. Accordingly, testing for the presence of fibrosis or presence of myofibroblasts may include one or all of the above methodologies. The positive detection of fibrosis would then be indicated for treatment with trametinib under the methods of treatment provided herein.

Methods

We tested several molecules for their impact on pathways we believe to be implicated in adhesion. For example, several kinase inhibitors were tested that we believed would implicate and effect the formation of adhesions. However, the non-published data was ineffective. Accordingly, we have omitted data for the compounds that were ineffective.

Reagents and Antibodies

All reagents, unless otherwise specified, were purchased from Sigma (St. Louis, MO). Other reagents were SuperSignal West Pico or Femto Chemiluminescent Substrate and Coomassie Protein Assay (Pierce, Chicago, IL); PVDF membrane (Roche Diagnostics, Basel, Switzerland); #4904, MEK1/2 #4694, phospho-MEK1/2 #9154, phospho-Smad2 #3108, phospho-Smad2 (Ser 245/250/255) #3104, p44/42 MAPK (Erk1/2) #9107, phospho-p44/42 MAPK (Erk1/2) #4370, antibody to the EDA isoform of fibronectin (FNEDA) [11] and αSMA antibody #ab5694 (Abcam, Cambridge, MA); ImmunoPure peroxidase-conjugated secondary antibodies (Pierce Antibody Products, Waltham, MA); MEK1/2 inhibitor U0126 (Selleck Chemicals, Houston, TX).

Isolation and Culture of Rat Peritoneal Mesothelial Cells (RPMCs)

The experiments in this study were approved by the Institutional Animal Care and Use Committee at Thomas Jefferson University, and were performed in accordance with the National Institutes of Health guidelines for the care and handling of laboratory animals. RPMCs were isolated and cultured as described previously [12]. Briefly, Sprague Dawley rats weighing 150 g-250 g, purchased from Jackson Laboratory, were injected intra-peritoneally with 30 ml of 0.25% trypsin/2.21 mM EDTA under Isoflurane anesthesia and were kept on the metal pad warmed to 37° C. for one hour; after which the abdominal fluid was collected and centrifuged at 300 g for 10 minutes. The isolated pelleted cells were re-suspended and cultured in DMEM/F12 medium supplemented with 10% (v/v) FBS at 37° C. in a humidified atmosphere of 5% CO2 in air. The RPMCs, from the fourth to seventh passages (split ratio 1:4), at 90% confluence were used for the experiments. The cells were treated either with 10 ng/ml of TGF-β1 (R&D systems) alone, or with TGF-β1 and the MEK1/2 inhibitor, Trametinib (2 or 5 nM).

Cecal Abrasion Model

Equal numbers of male and female C57BL/6 mice (18-25 g, 8-10 weeks of age, Jackson Laboratories, Bar Harbor, Maine) were used in initial experiments while only male mice were used in the drug escalation studies because they sustained greater accumulations of fibrotic tissue (data not shown). Mice were allowed to acclimate in the animal facility for at least one week prior to surgery, given free access to standard chow and water and a 12-h light-dark cycle in standard acrylic cages with wood chip bedding. Animals were randomly assigned into either an experimental group (laparotomy and cecal abrasion) or a control group (laparotomy only).

Briefly, mice underwent induction and maintenance anesthesia with 1-3% isofluorane with supplemental oxygen. After adequate sedation was achieved, mice were weighed and 0.1 mg/kg subcutaneous Buprenex (Hospira, Inc., Lake Forest, IL) was administered to ensure analgesia. The ventral surface was clipped along the midline and the skin was sterilized with betadine. A 2 cm midline incision was made subxiphoid to avoid injuring the bladder and the cecum was identified and externalized. The anti-mesenteric side of the cecum was gently swiped 30 times with gauze then returned to the abdomen. The incision was closed with a double layer of sutures with 2-0 silk [13]. To characterize adhesion formation, mice were placed into groups, each with 6 males and 6 females which were necropsied at 1, 2, 5, 8, 11, 14, 17, 21 and 23 days post-surgery. Each time point also contained 2 male mice and one female mouse as controls. In the drug escalation study, laparotomy and cecal abrasion were carried out as above as well as sub-dermal placement of the osmotic pumps.

Drug Treatment with Trametinib

Animals were treated with 3 different doses of the drug trametinib in a dose escalation study. Groups of 5 animals were given 0.1, 1.0 or 3.0 mg/kg animal weight of drug/day via osmotic pumps (Alzet Osmotic Pump 1002, Cupertino, CA) for eight days prior to sacrifice. The volume delivered/day was 6 ul of drug. Control mice underwent induction with anesthesia and laparotomy only. In addition, 5 animals underwent laparotomy and placement of the osmotic pumps which were filled with "drug vehicle (DMSO)" alone i.e., no drug. After 8 days of drug treatment, mice were euthanized under isofluorane anesthesia followed by cervical dislocation. Adhesions were examined by two independent practitioners. The entire large intestine and cecum were removed and partitioned for histology and immunofluorescence microscopy.

Histology

Bowel and abdominal wall involved in the adhesion were removed en bloc and fixed in 4% buffered formalin. Abdominal wall from control mice was also taken as a control. Tissues were dehydrated, embedded in paraffin and sectioned at either 5 or 10 microns (u). Sections were de-paraffinized in a graded ethanol series and stained with Masson's Trichrome. Photographs were taken with a Zeiss light microscope equipped with a Nikon digital camera.

Immunofluorescence

Intestinal tissue was placed in Tissue-Tek O.C.T. Compound (Sakura Finetek, Torrance, CA) and immediately frozen in liquid nitrogen. Frozen sections were cut at either 5 or 10 u, allowed to adhere to albumin-coated slides and then washed with PBS, followed by double staining with goat anti-SMA polyclonal antibody (1:100, Abcam Inc.), and anti-FNEDA antibody (Anna-Karin Olsson) overnight at 4° C. After washing 3× with PBS, species matched Alexa-Fluor secondary antibodies (Invitrogen) were added and incubated for 1 hr. at room temperature followed by 3 washes with PBS. Slides were mounted with DAPI Fluoromount-G (Southern Biotech) and fluorescence images were taken with a Zeiss epi-fluorescence microscope. Controls included omitting the primary antibody and replacing it either with saline or indifferent IgG from a control animal and omission of the secondary antibody. In all instances, controls were either negative or showed very slight non-specific staining with the secondary antibody alone.

Western Blotting Analysis

RPMCs were lysed in ice-cold modified RIPA buffer with protease inhibitor cocktail (50 mM/L Tris-HCl, 1% NP-40, 0.25% Na-deoxycholate, 150 mM/L NaCl, 1 mM/L EDTA, 1 mmol/L phenylmethyl sulfonyl fluoride, 1 mM/L sodium orthovanadate, 1 mM/L NaF, pH 7.4). Equivalent amounts of homogenate (50 μg/well), determined by Coomassie blue assay, were separated by sodium dodecyl sulfate polyacrylamide gel electrophoresis (SDS-PAGE), transferred to either nitrocellulose or PVDF membranes, and detected by SuperSignal West Femto or Pico chemiluminescence.

REFERENCES

1. Tomasek J J, Gabbiani G, Hinz B, Chaponnier C, Brown R A (2002) Myofibroblasts and mechano-regulation of connective tissue remodelling. Nature reviews Molecular cell biology 3 (5):349-363. doi:10.1038/nrm809
2. Roberts A B, Sporn M B, Assoian R K, Smith J M, Roche N S, Wakefield L M, Heine U I, Liotta L A, Falanga V, Kehrl J H, et al. (1986) Transforming growth factor type beta: rapid induction of fibrosis and angiogenesis in vivo and stimulation of collagen formation in vitro. Proc Natl Acad Sci USA 83 (12):4167-4171
3. Ignotz R A, Massague J (1986) Transforming growth factor-beta stimulates the expression of fibronectin and collagen and their incorporation into the extracellular matrix. J Biol Chem 261 (9):4337-4345
4. Ignotz R A, Endo T, Massague J (1987) Regulation of fibronectin and type I collagen mRNA levels by transforming growth factor-beta. J Biol Chem 262 (14):6443-6446
5. Jin X, Zimmers T A, Perez E A, Pierce R H, Zhang Z, Koniaris L G (2006) Paradoxical effects of short- and long-term interleukin-6 exposure on liver injury and repair. Hepatology 43 (3):474-484. doi:10.1002/hep.21087
6. Jin X, Zhang Z, Beer-Stolz D, Zimmers T A, Koniaris L G (2007) Interleukin-6 inhibits oxidative injury and necrosis after extreme liver resection. Hepatology 46 (3):802-812. doi:10.1002/hep.21728
7. Jin X, Zimmers T A, Zhang Z, Pierce R H, Koniaris L G (2010) Interleukin-6 is an important in vivo inhibitor of intestinal epithelial cell death in mice. Gut 59 (2):186-196. doi:10.1136/gut.2008.151175 gut.2008.151175 [pii]
8. Falk P, Bergstrom M, Palmgren I, Holmdahl L, Breimer M E, Ivarsson M L (2009) Studies of TGF-beta(1-3) in serosal fluid during abdominal surgery and their effect on in vitro human mesothelial cell proliferation. J Surg Res 154 (2):312-316. doi:10.1016/j.jss.2008.05.01250022-4804(08)00359-4 [pii]
9. Cheong Y C, Shelton J B, Laird S M, Richmond M, Kudesia G, Li T C, Ledger W L (2002) IL-1, IL-6 and TNF-alpha concentrations in the peritoneal fluid of women with pelvic adhesions. Hum Reprod 17 (1):69-75
10. Jin X, Ren S, Macarak E, Rosenbloom J (2016) Pathobiological mechanisms of peritoneal adhesions: The mesenchymal transition of rat peritoneal mesothelial cells induced by TGF-beta1 and IL-6 requires activation of Erk1/2 and Smad2 linker region phosphorylation. Matrix biology: journal of the International Society for Matrix Biology. doi:10.1016/j.matbio.2016.01.017
11. Femel J, Huijbers E J, Saupe F, Cedervall J, Zhang L, Roswall P, Larsson E, Olofsson H, Pietras K, Dimberg A, Hellman L, Olsson A K (2014) Therapeutic vaccination against fibronectin E D-A attenuates progression of metastatic breast cancer. Oncotarget 5 (23):12418-12427. doi: 10.18632/oncotarget.2628
12. Liu Q, Zhang Y, Mao H, Chen W, Luo N, Zhou Q, Yu X (2012) A crosstalk between the Smad and JNK signaling in the TGF-beta-induced epithelial-mesenchymal transition in rat peritoneal mesothelial cells. PLoS One 7 (2):e32009. doi:10.1371/journal.pone.0032009 PONE-D-11-21744 [pii]
13. Panahi F, Sadraie S H, Khoshmohabat H, Shahram E, Kaka G, Hosseinalipour M (2012) Macroscopic and pathological assessment of methylene blue and normal saline on postoperative adhesion formation in a rat cecum model. International journal of surgery (London, England) 10 (9):537-541. doi:10.1016/j.ijsu.2012.08.009
14. Xu X, Rivkind A, Pappo O, Pikarsky A, Levi-Schaffer F (2002) Role of mast cells and myofibroblasts in human peritoneal adhesion formation. Annals of surgery 236 (5):593-601. doi:10.1097/01.sla.0000033037.13104.c4
15. Postlethwaite A E, Shigemitsu H, Kanangat S (2004) Cellular origins of fibroblasts: possible implications for organ fibrosis in systemic sclerosis. Current opinion in rheumatology 16 (6):733-738
16. Bellini A, Mattoli S (2007) The role of the fibrocyte, a bone marrow-derived mesenchymal progenitor, in reactive and reparative fibroses. Lab Invest 87 (9):858-870. doi:3700654 [pii] 10.1038/labinvest.3700654
17. Thiery J P, Sleeman J P (2006) Complex networks orchestrate epithelial-mesenchymal transitions. Nat Rev Mol Cell Biol 7 (2):131-142. doi:nrm1835 [pii] 10.1038/nrm1835
18. Thiery J P, Acloque H, Huang R Y, Nieto M A (2009) Epithelial-mesenchymal transitions in development and disease. Cell 139 (5):871-890. doi:10.1016/j.cell.2009.11.007 S0092-8674(09)01419-6 [pii]
19. Kalluri R, Neilson E G (2003) Epithelial-mesenchymal transition and its implications for fibrosis. The Journal of clinical investigation 112 (12):1776-1784. doi:10.1172/jci20530
20. Duscher D, Maan Z N, Wong V W, Rennert R C, Januszyk M, Rodrigues M, Hu M, Whitmore A J, Whittam A J, Longaker M T, Gurtner G C (2014) Mechanotransduction and fibrosis. Journal of biomechanics 47 (9): 1997-2005. doi: 10.1016/j.jbiomech.2014.03.031
21. Bhattacharyya S, Wei J, Varga J (2011) Understanding fibrosis in systemic sclerosis: shifting paradigms, emerging opportunities. Nature reviews Rheumatology 8 (1): 42-54. doi:10.1038/nrrheum.2011.149
22. Macarak E, Lotto C, Kolganti D, Jin X, Wermuth P, Olsson A-K, Montgomery M and Rosenbloom J. (2018) Trametinib prevents mesothelial-mesenchymal. transition and ameliorates abdominal adhesion. Journal of Surgical Research (In Press, July 2018).

What is claimed is:

1. A method of reducing the occurrence of excessive fibrin formation in a patient consisting of administering to said patient one effective dose of Trametinib (GSK1120212) sufficient to reduce the fibrin formation prior to a surgical procedure, and a further dose of the Trametinib (GSK1120212) for seven days after said surgical procedure daily, wherein the effective dose of Trametinib (GSK1120212) is between 0.01 mg to 1.5 mg.

2. The method of claim 1, in which the excessive fibrin formation in said patient is an abdominal adhesion caused by an abdominal surgery.

3. The method of claim 1, wherein the effective dose of Trametinib (GSK1120212) is between 0.01 mg to 1.0 mg.

* * * * *